United States Patent
Sakiyama et al.

[11] Patent Number: 6,063,023
[45] Date of Patent: May 16, 2000

[54] MEASURING ENDOSCOPE SYSTEM

[75] Inventors: Katsunori Sakiyama, Akiruno; Masayoshi Yokota, Hachioji, both of Japan

[73] Assignee: Olympus Optical Co., Ltd., Japan

[21] Appl. No.: 09/036,216

[22] Filed: Mar. 6, 1998

[30] Foreign Application Priority Data

Mar. 12, 1997 [JP] Japan ................................. 9-058114

[51] Int. Cl.[7] ................................................. A61B 1/055
[52] U.S. Cl. ...................... 600/118; 600/117; 600/166; 600/172; 600/175
[58] Field of Search ............................. 600/111, 117, 600/118, 166, 175, 172, 136; 348/45, 65, 71, 74, 75

[56] References Cited

U.S. PATENT DOCUMENTS

| | | |
|---|---|---|
| 4,702,229 | 10/1987 | Zobel . |
| 4,873,572 | 10/1989 | Miyazaki ................................. 600/111 |
| 4,895,431 | 1/1990 | Tsujiuchi ................................... 348/45 |
| 4,935,810 | 6/1990 | Nonami ..................................... 348/45 |
| 5,305,098 | 4/1994 | Matsunaka ................................ 348/45 |
| 5,313,306 | 5/1994 | Kuban ....................................... 348/65 |
| 5,432,543 | 7/1995 | Hasegawa ................................ 348/45 |
| 5,469,254 | 11/1995 | Konomura ................................. 348/65 |
| 5,603,687 | 2/1997 | Hori ......................................... 600/111 |
| 5,711,756 | 1/1998 | Chikama .................................. 600/172 |
| 5,720,706 | 2/1998 | Takahashi ............................... 600/111 |
| 5,776,050 | 7/1998 | Chen ......................................... 348/65 |
| 5,860,912 | 1/1999 | Chiba ........................................ 348/45 |

FOREIGN PATENT DOCUMENTS

| | | |
|---|---|---|
| 62-80768 | 4/1987 | Japan . |
| 64-26813 | 1/1989 | Japan . |

Primary Examiner—John P. Leubecker
Attorney, Agent, or Firm—Ostrolenk, Faber, Gerb & Soffen, LLP

[57] ABSTRACT

A measuring endoscope system including an optical adaptor freely attachable or detachable to or from a distal portion of an endoscope and having two objective lenses. Two images are taken by the two objective lenses and are formed at different positions on an imaging device incorporated in a main endoscope unit. A measuring unit for reading information from a recording medium on which optical data specific to the optical adaptor is recorded, correcting the optical data on the basis of an error in position of an imaging system in the main endoscope unit, performing coordinate conversion on images used for measurement on the basis of the corrected optical data, and calculating three-dimensional coordinates of any points by matching the two images having undergone coordinate conversion.

24 Claims, 19 Drawing Sheets

MEASURING ENDOSCOPE SYSTEM

BACKGROUND OF THE INVENTION

1. Field of the Invention

The present invention relates to a measuring endoscope system for forming two images of an object to be measured, which are taken by two objective lenses, at different positions on an imaging device incorporated in a main endoscope unit, processing the data of the endoscopic images, and carrying out measurement.

2. Description of the Related Art

A stereoscope endoscope using one CCD has been disclosed in Japanese Unexamined Patent Publication No. 64-26813 in the past. Japanese Unexamined Patent Publication No. 62-80768 has disclosed a means for correcting geometric distortions in images produced to realize stereoscope by utilizing a parallax caused by observing an object from right and left points, and for upgrading the level of matching from coarse matching performed at a low resolution to matching performed at a high resolution by predicting relative distortions in the images for realizing stereoscope.

Although the Japanese Unexamined Patent Publication No. 64-26813 has disclosed a stereoscope endoscope utilizing one CCD, no mention is made of a means for measuring an object.

The Japanese Unexamined Patent Publication No. 62-80768 has disclosed a technique for correcting geometric distortions in images for realizing stereoscope and grading the level of matching from coarse matching performed at a low resolution to matching performed at a high resolution by predicting relative distortions in the images for realizing stereoscope, but it has not described a measuring method which takes into account the uncertainty in the characteristics of lenses which occurs when one optical adaptor is exchanged for another.

A known stereoscopy measuring apparatus comprises two imaging systems which take images for realizing stereoscope, a capture circuit for fetching the data of the stereoscopic images into a computer, and a computer for processing the image data. The two imaging systems may be realized with two independent cameras or may be, as described in the Japanese Unexamined Patent Publication No. 64-26813, realized with one imaging device for imaging the stereoscopic images.

This kind of stereoscope measuring apparatus cannot achieve measurement with high precision unless distortions in images caused by lenses are dealt with. The lenses cannot therefore be heedlessly replaced with new ones. Even when a stereoscopic measurement method is adapted to an endoscope, it is preferred that a plurality of types of optical adaptors are made available for alternate use so that not only stereoscopic measurement can be performed, but also observation through a single lens can be achieved. However, for stereoscopic measurement, an endoscope dedicated to stereoscopic measurement must be employed because of the image distortions caused by the lenses.

Normally, optical adaptors are different from one another in terms of optical characteristics. Moreover, the position of a CCD incorporated in a main video endoscope unit is uncertain. The uncertainty can be a cause of critical error in measurement. For eliminating the error, it is necessary to associate the optical adaptors used for measurement with video endoscopes on a one-to-one basis, acquire optical data, and correct image data.

However, if a video endoscope is put on sale in combination with an associated optical adaptor used for measurement, a user who does not intend to carry out measurement procedures will find the endoscope expensive because of the unnecessary optical adaptor for the user. However, if a video endoscope is not marketed in combination with an associated optical adaptor used for measurement, problems arise that an optical adaptor used for measurement cannot be additionally purchased and used in combination with a main video endoscope unit.

On the side of a manufacturer, there is a problem that since an optical adaptor must be attached to a main video endoscope unit in order to acquire data, a manufacturing process becomes complex and cost increases accordingly. Consequently, the measuring endoscope system is expensive for users.

SUMMARY OF THE INVENTION

An object of the present invention is to improve the measuring precision offered by a measuring endoscope system for carrying out measurement by processing data of endoscopic images taken by two objective lenses.

Moreover, another object of the present invention is to provide an inexpensive measuring endoscope capable of carrying out measurement by processing data of endoscopic images taken by two objective lenses.

Furthermore, another object of the present invention is to expand the range of diverse usages of a measuring endoscope system by making a plurality of optical adaptors attachable or detachable to or from a distal endoscope part.

In short, the optical adaptors are made freely attachable or detachable. A normal single-lens optical adaptor is also usable.

Yet another object of the present invention is to enable stereoscopic measurement by combining an optical adaptor for stereoscopic measurement with a video image endoscope for normal observation and employing optical data specific to the optical adaptor.

A measuring endoscope system in accordance with the present invention comprises: an optical adaptor freely attachable and detachable to or from a distal part of an endoscope and includes two objective optical systems; an endoscope in which two images taken by the two objective optical systems are formed at different positions on an imaging device incorporated in a main endoscope unit; and a measuring means for, when carrying out measurement by processing data of endoscopic images, at least reading information from a recording medium, on which optical data specific to the optical adaptor is recorded, correcting the optical data on the basis of a positional error of an imaging system included in the main endoscope unit, performing coordinate conversion on images used for measurement on the basis of the corrected optical data, and calculating three-dimensional coordinates of corresponding points by matching the two images having undergone coordinate conversion.

DESCRIPTION OF THE PREFERRED EMBODIMENTS

Figure 1:
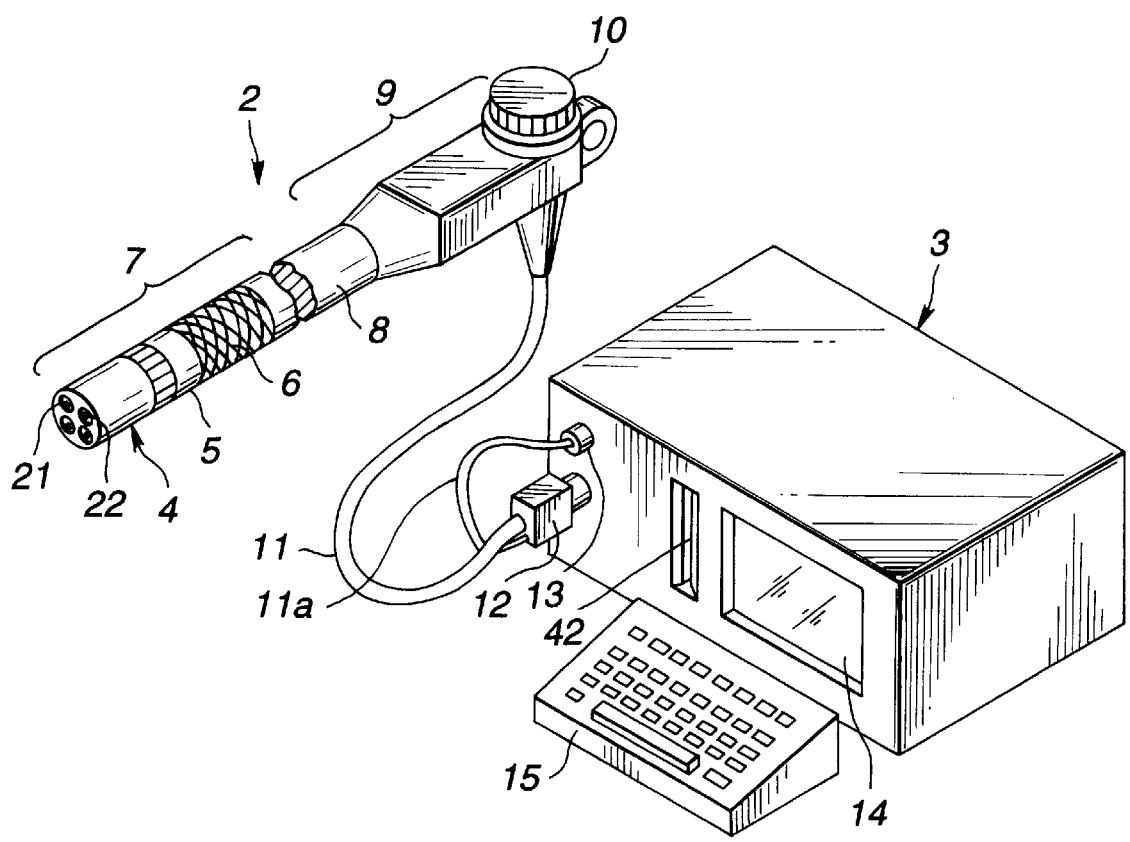
FIG. 1 is a diagram showing the overall configuration of a measuring endoscope system in accordance with the first embodiment of the present invention.
Figure 2:
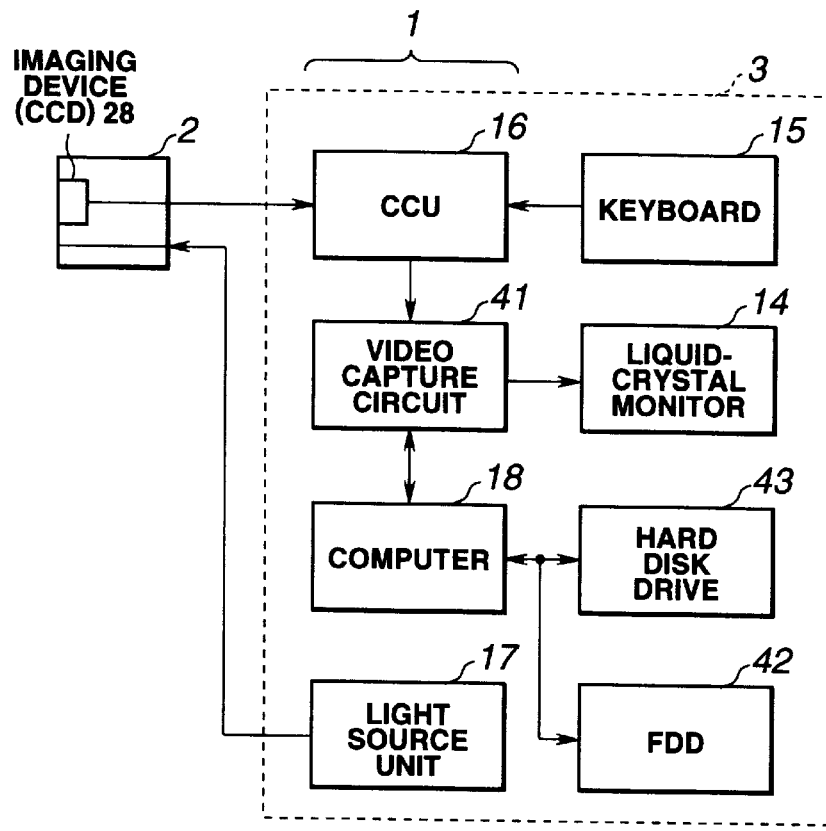
FIG. 2 is a block diagram of the measuring endoscope system shown in FIG. 1.

As shown in FIGS. 1 and 2, a measuring endoscope system 1 comprises a video endoscope (hereinafter referred simply to as an endoscope) 2 in which an imaging device is incorporated, and a measuring apparatus 3 that is a measuring means.

The endoscope 2 has an optical adaptor 4, which has two systems of lenses, attached thereto, and includes an insertion unit 7 in which the imaging device is incorporated, an operation unit 9 for use in angling the insertion unit 7, a universal cable 11, a light source connector 12, and a camera control connector 13.

The measuring apparatus 3 includes a camera control unit (hereinafter abbreviated to a CCU) 16 for converting an image signal sent from the endoscope 2 into a video signal such as an NTSC signal, a video capture circuit 41 for converting the video signal into a digital still image signal, a computer 18 for processing image data represented by a digital image signal sent from the video capture circuit 41, a liquid-crystal monitor 14 for displaying a processing menu and processed images, a hard disk drive (hereinafter abbreviated to a HDD) 43 for recording or reproducing control processing information or image information on or from a recording medium, a floppy disk drive (hereinafter abbreviated to an FDD) 42, a keyboard 15 for use in entering data, and a light source unit 17 for supplying illumination light for observation to the endoscope 2.

Prior to the detailed explanation of the components and operations of the measuring endoscope system 1 in accordance with this embodiment, the system 1 will be outlined below.

Figure 5:
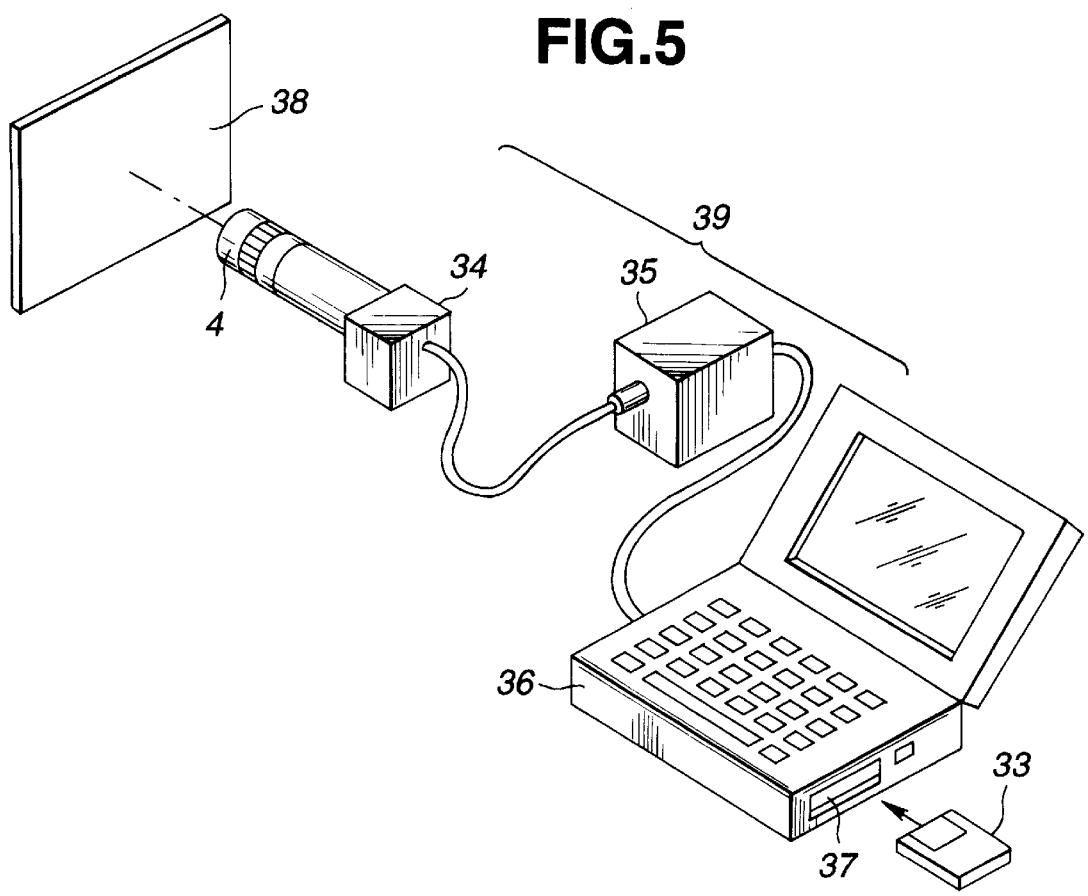
FIG. 5 is a diagram showing a state in which optical data is acquired using a production measurement jig in combination with the measuring endoscope system shown in FIG. 1.
Figure 6A:
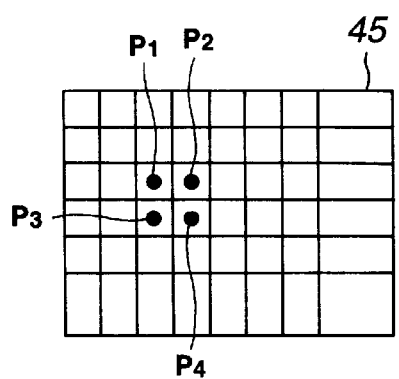
FIG. 6A is a diagram showing the arrangement of pixels of an image whose geometric distortion has not been corrected by the measuring endoscope system shown in FIG. 1.
Figure 6B:
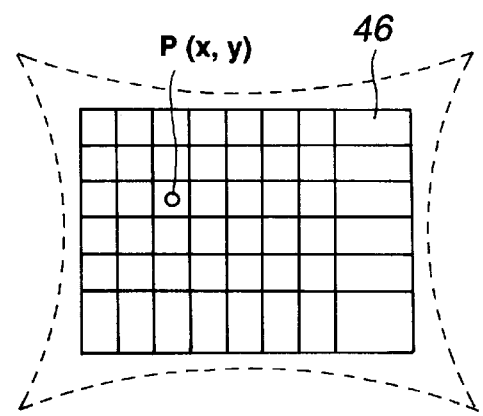
FIG. 6B is a diagram showing the arrangement of pixels of the image whose geometric distortion has been corrected by the measuring endoscope system shown in FIG. 1.

In order to obtain optical characteristic data of the optical adaptor 4, the optical adaptor 4 is attached to a master imaging unit 34 as shown in FIG. 5. Master imaging unit 34 can be associated with any number of different optical adaptors at various production steps, including a production measurement jig 39, and has an imaging device incorporated therein. Master imaging unit 34 acquires the below listed Optical data items (a) to (d) which are specific to each optical adaptor 4. The optical data items are recorded on a floppy disk (hereinafter abbreviated to an FD) 33 (See FIG. 5) that is a recording medium. The FD 33 on which the specific optical data items are recorded and the optical adaptor are associated with each other, and are thereafter handled as a pair.

The specific optical data items are listed below:
(a) a geometric distortion correction table used to correct geometric distortions caused by two optical systems;
(b) focal lengths from two systems of lenses;
(c) a distance between optical axes of two lenses; and
(d) position information of two images relative to the master imaging unit.

The optical adaptor 4 having its specific optical data acquired as described above is then attached to the endoscope 2. By following the processing steps (1) to (8) described below, various kinds of dimension measurements can be achieved.

(1) Reading optical data items (a) to (d) from the FD 33.
(2) Using the system 1 to image a white object.
(3) Calculating a difference in position between images produced by attaching the optical adaptor 4 to the endoscope 2 on the basis of the data item (d) and the image data acquired at step (2).
(4) Creating a conversion table used for correcting geometric distortions occurring in the endoscope 2 on the basis of the data acquired at step (3) and the data acquired at step (1).
(5) Imaging an object to be measured by means of the endoscope 2, and acquiring image data.
(6) Performing coordinate conversion on the image data acquired at step (5) on the basis of the table created at step (4).
(7) Calculating the three-dimensional coordinates of points by matching the two image data items having undergone coordinate conversion.
(8) Carrying out various kinds of dimension measurements on the basis of the three-dimensional coordinates.

By carrying out the above processing, the endoscope system 1 can measure an object with high precision. The configuration and operation of the system will be explained in detail.

Figure 3:
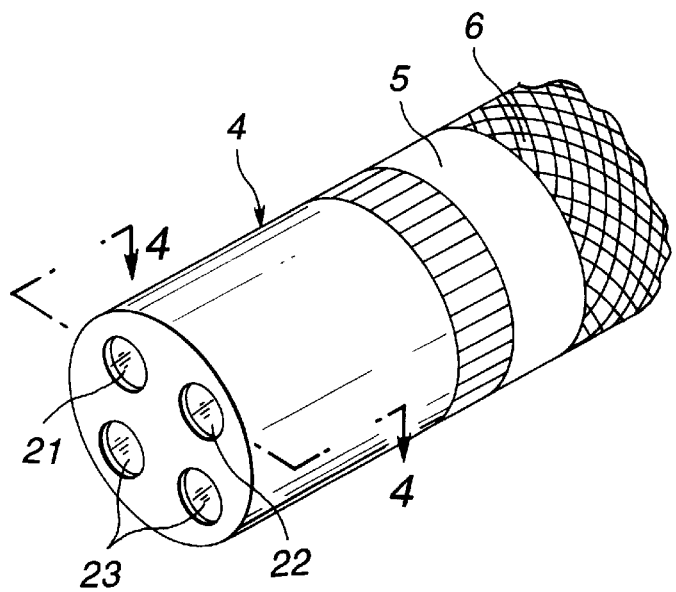
FIG. 3 is an enlarged view showing a distal part of an insertion unit of an endoscope included in the measuring endoscope system shown in FIG. 1.
Figure 4:
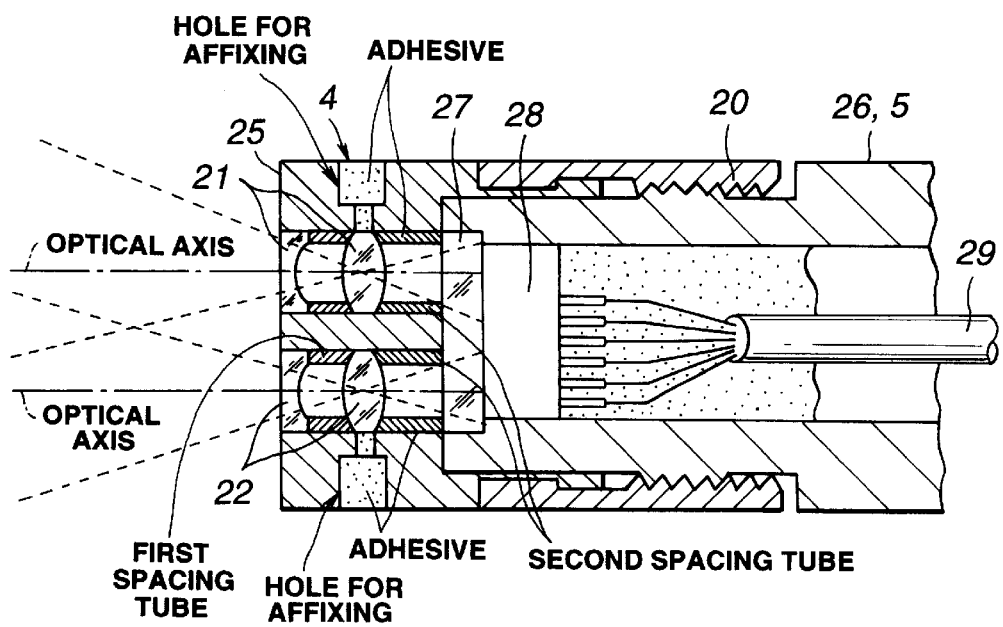
FIG. 4 is a sectional view of the distal part shown in FIG. 3 take along line 4—4.

As shown in FIGS. 1, 3, and 4, the insertion unit 7 of the endoscope 2 consists of the optical adaptor 4 freely attachable or detachable to or from a distal endoscope part 5, a cover glass 27 and imaging device 28 incorporated in the distal part 5, a bending portion 6 making it possible to angle the distal endoscope part 5 using an angulation knob 10 on the operation unit 9, and a flexible part 8 linking the bending portion 6 and operation unit and capable of being freely bent.

The optical adaptor 4 consists of a main optical adaptor unit 25, two illumination windows 23 formed in the end surface of the main unit 25, a right objective lens 21 and left objective lens 22 that are two objective lenses forming two objective optical systems, and a threaded portion 20. With the threaded portion 20, the optical adaptor 4 is freely detachably attached to the main endoscope unit 26. Images taken by the right objective lens 21 and left objective lens 22 are formed at different positions on one imaging device 28 incorporated in the distal endoscope part 5.

The optical adaptor 4 has hole for affixing lenses 21, 22 in adaptor unit 25. The holes for affixing are filled with an adhesive, whereby the side surface of the objective lens 21 and 22 are firmly affixed. As a result, both the objective lenses 21 and 22 are firmly affixed to the main unit 25. Since the objective lenses 21, 22 are firmly affixed to the main unit 25, a backlash in the circumferential direction of the lenses is prevented. Consequently, the deterioration of the precision of measurements deriving from a difference in image formation position can be prevented. In prior art endoscopes, a convex lens is used for the objective lens 22 and is sandwiched between a first spacing tube and second spacing tube but is not affixed using an adhesive. If the prior art endoscope experiences an impact, this causes the convex lens to be displaced by several micrometers in the circumferential direction, and leads to the deterioration of measurement precision.

A light guide fiber bundle that is not shown and a signal line 29 extend from the imaging device 28 in the distal endoscope part and pass through the universal cable 11 connected to the operation unit 9 of the endoscope 2. The light guide fiber bundle is spliced to the light source connector 12. The signal line 29 extends from the imaging device 28 and is spliced to the CCU connector 13.

The FD 33 (FIG. 5) on which optical data specific to the optical adaptor 4 is recorded, is inserted into an FDD 42 of the measuring apparatus 3, whereby the optical data can be retrieved. Image signals representing images taken by the right objective lens 21 and left objective lens 22 of the endoscope 2 are converted into video signals by the CCU 16 in the measuring apparatus 3, displayed as images of an object to be measured on the liquid-crystal monitor 14, and also recorded in a memory in the computer 18. The computer 18 performs measurement on the object to be measured on the basis of the retrieved optical data specific to the optical adaptor 4.

As shown in FIG. 5, the production measurement jig 39 consists of a master imaging unit 34 to which the optical adaptor 4 can be attached and which has the same structure as the distal endoscope part 5, a CCU 35 which is linked to a signal line extending from the unit 34, an FDD 37 which the FD 33 data s loaded, a personal computer 36 for processing image data sent from the CCU 35, and a test chart 38 used to analyze the optical characteristics of an optical adaptor.

For acquiring optical data by means of the production measurement jig 39, first, as shown in FIG. 5, the optical adaptor 4 is attached to the master imaging unit 34. Images of the chart 38 are taken via the optical adaptor 4. Resultant image data is processed by the personal computer 36, whereby the aforesaid data items (a) to (d) are produced and recorded on the FD 33.

The optical data items specific to the optical adaptor 4 will be described more particularly. To begin with, the geometric distortion correction table (a) will be described.

In general, an image taken by a system of lenses suffers from an optical distortion. The distortion causes a critical error in measurement. Coordinate conversion can cancel the distortion. Coordinate conversion may be carried out with the center of an optical axis as a center. For more accurate correction, the center of a geometric distortion caused by an optical system is employed. The geometric distortion correction table used to correct geometric distortions in two images may be provided as separate tables associated with a right image and left image respectively, or may be provided as one table. The geometric distortion correction table that is provided as one table will be described in conjunction with FIGS. 6A to 7B.

In FIGS. 6A, 6B, 7A, and 7B, points p1 to p4 in an image screen 45 indicate pixels not having undergone coordinate conversion. When coordinate conversion is performed on the points p1 to p4 by expressing the points as functions of x and y coordinates in the form of f(x, y), the points p1 to p4 shall be converted into points p1' to p4'. The coordinate values defining the points p1' to p4' are not always integers but may be real numbers. For displaying pixels in an after-conversion screen 46 on the liquid-crystal monitor, the coordinates (X, Y) of the pixels P(X, Y) must be converted into integers serving as pixel values.

In order to convert the coordinate values into integers, correction is carried out using a weight table which includes weights W1 to W4. That is to say, for each pixel in an after-conversion screen 46, image data items of four pixels defined with coordinates predicted from an optical geometric distortion observed in an image screen are multiplied by the weights W1 to W4. Thus, pixel data P(X, Y) is calculated for each pixel in the after-conversion screen 46.

For calculating after-conversion coordinates x' and y', which result from coordinate conversion, as the function f ( x, y ), the following expressions are employed:

$$x' = k1x\,(a_{00} + a_{30}x^3 + a_{12}xy^2 + a_{50}x^5 + a_{32}x^3y^2 + a_{14}xy^4 + a_{70}x^7 + a_{52}x^5y^2 + a_{34}x^3y^4 + a_{16}xy^6) \quad (1)$$

$$y' = k2x\,(b_{00} + b_{21}x^2y + b_{03}y^3 + b_{41}x^4y + b_{23}x^2y^3 + b_{05}y^5 + b_{61}x^6y + b_{43}x^4y^2 + b_{25}x^2y^5 + b_{52}x^2y^5 + b_{07}y^7) \quad (2)$$

Coefficients $a_{nm}$ and $be_{nm}$ are calculated in relation to the linearity of a grid image of the test chart 38 (FIG. 5). k1 and k2 are coefficients used to match magnifications of two images and functions of focal lengths fR and fL.

By assigning the x and y coordinates of the points P1 to P4 to the expansion of f(x, y), coordinates (x', y') defining the points p1'(x', y') to p4'(x', y') are calculated. The x' and y' coordinate values are, as mentioned above, not always integers. The weights W1 to W4 listed in the weight table are used for correction. Thus, pixel data items of after-conversion coordinates ( X, Y ) that are integers are calculated.

For example, a point at a corner of the image screen is regarded as an origin. The coordinates of the four points p1' to p4' in the after-conversion screen 46 (FIG. 7B), which provide the pixel data P(X, Y), are indicated with (x', y'). The x coordinate of the coordinates (x, y) of the left upper point present invention out of the four points ( x, y ) to (x+1, y+1) in the image screen corresponding to the four points p1' to p4' in the after-conversion screen is indicated with QX(X, Y), and the y coordinate thereof is indicated with QY(X, Y). The calculated x coordinate QX(X, Y) and y coordinate QY(X, Y) are listed in a coordinate reference table included in a geometric distortion correction table and then stored in the FD 33.

Figure 7A:
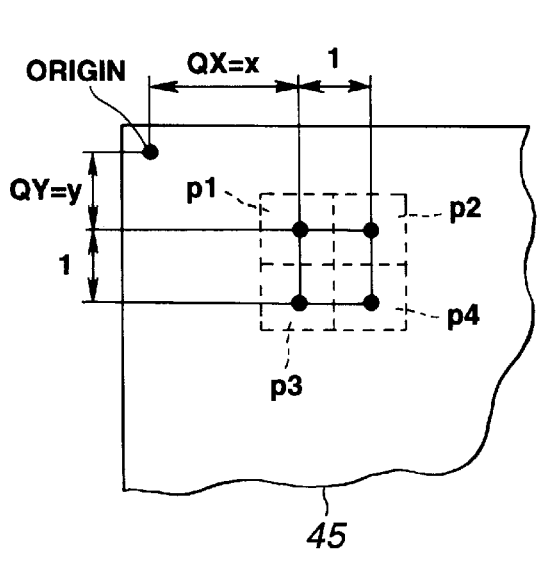
FIG. 7A is a diagram showing pixels of an image that has not been corrected by the measuring endoscope system shown in FIG. 1.
Figure 7B:
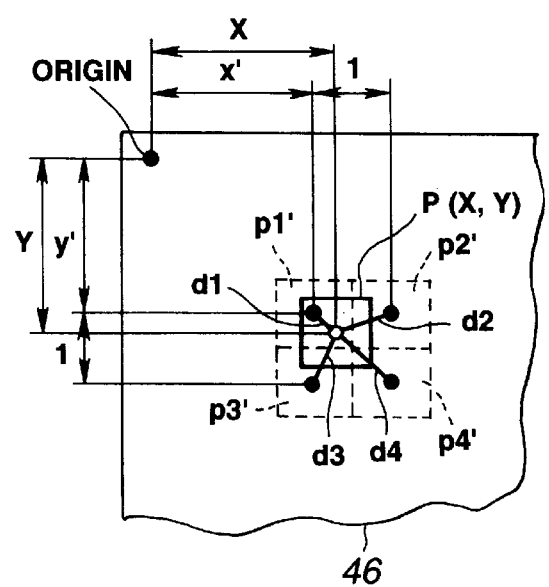
FIG. 7B is a diagram showing pixels of the image that has been corrected by the measuring endoscope system shown in FIG. 1.

Pixel data P(X, Y) of each pixel at a position defined with coordinates (X, Y) indicated with integers, which results from conversion, is calculated by multiplying the coordinates of the points p1' to p4' by the weights W1 to W4. However, as shown in FIGS. 7A and 7B, assuming that a distance from the point p1', p2', p3' or p4' to the pixel position P(X, Y) is dn, the following relationship is established:

$$S = d1 + d2 + d3 + d4 \quad (3)$$

Based on the expression (3), the weights are defined as follows:

$$W1 = d1/S$$
$$W2 = d2/S$$
$$W3 = d3/S$$
$$W4 = d4/S \quad (4)$$

Using the expressions (4), the pixel data P(X, Y) is defined as follows:

$$P(X, Y) = W1 \times p1' + W2 \times p2' + W3 \times p3' + W4 \times p4' \quad (5)$$

The weights W1, W2, W3, and W4 are listed in relation to all pixel points (X, Y) in the after-conversion screen in the form of a weight table, and recorded on the FD 33 together with the x and y coordinates QX(X, Y) and QY(X, Y) listed in the coordinate reference table.

Next, the optical data items (b) to (d) specific to an optical adaptor 4 will be described.

In order to determine data item (b) measurements are taken and recorded of the focal lengths from two systems of lenses; a focal length fR from a system of lenses generating a right image and a focal length fL from a system of lenses generating a left image.

In order to determine data item (c) measurements are taken and recorded of the coordinates of the optical axes of the two systems of lenses; the coordinates XR and YR of the optical axis of a system of lenses generating the right image and the coordinates XL and YL of the optical axis of a system of lenses generating the left image.

In order to determine item (d) measurements are taken and recorded of the position information of two images relative to the master imaging unit (patterns of field shapes); luminance data detected along a reference line V (vertical line), PV(100, Yn) where Yn is 1, 2, 3, . . . 480, and luminance data detected along a reference line H (horizontal line), PH(Xn, 100) where Xn is 1, 2, 3, . . . 640.

Stereoscopic measurement performed by the measuring endoscope system 1 of this embodiment having the foregoing configuration will be described with reference to the flowcharts of FIGS. 8–13.

A stereoscopic measurement is measurement based on three-dimensional coordinates calculated using data items of right and left images that have a parallax between them and that are taken by the right objective lens 21 and left objective lens 22 incorporated in the optical adaptor 4.

Figure 8:
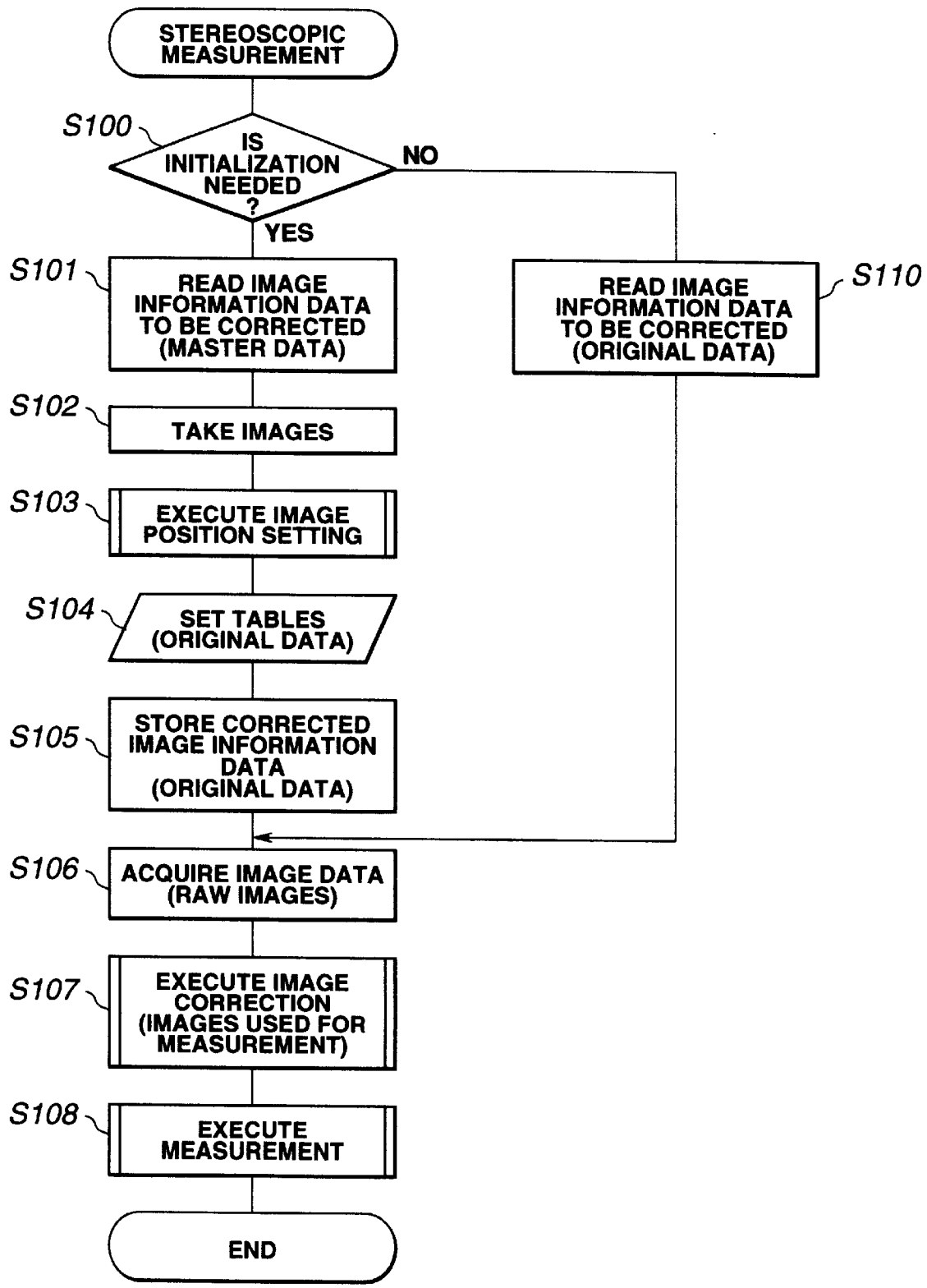
FIG. 8 is a flowchart describing a method of stereoscopic measurement performed by the measuring endoscope system shown in FIG. 1.

First, at step S100 in FIG. 8, it is checked whether or not initialization should be carried out. Specifically, when the measurement software has just been started up or when the optical adaptor 4 or endoscope has been exchanged, control is passed to a routine from step S101 to step S105 and initialization is executed. In any other case, control is passed to step S110 in which information data that has already been set is read as original data. Control is then passed to step S106.

At step S101, image data to be corrected is read. Specifically, optical data items (a) to (d) specific to the optical adaptor 4 are read from the FD 33 and used as master data.

At step S102, images of a white object are taken. Specifically, the white object is imaged by the measuring endoscope system 1 with the optical adaptor 4 attached thereto, and the image data items (a)–(d) of the white object are stored in a memory in the computer 18 via the video capture circuit 41 (See FIG. 2).

At step S103, a subroutine Image Position Setting (See FIG. 9A) that will be described later is executed. The subroutine calculates a magnitude of mismatch or a difference in coordinates between images derived from a difference in characteristics between the master imaging unit 34, which has acquired the optical data specific to the optical adaptor 4 in the course of manufacturing, and the endoscope 2.

At step S104, tables are set. That is to say, the data item (2) read at step S101, (the geometric distortion correction table used to correct geometric distortions in two kinds of images) is corrected according to the magnitude of mismatch or the difference in coordinates calculated at step S103. In other words, original data consisting of the weight table and coordinate reference table is created.

As the weight table, weights expressed as follows are listed:

$$W1'(X, Y) = W1(X + \Delta X, Y + \Delta Y)$$
$$W2'(X, Y) = W2(X + \Delta X, Y + \Delta Y)$$
$$W3'(X, Y) = W3(X + \Delta X, Y + \Delta Y)$$
$$W4'(X, Y) = W4(X + \Delta X, Y + \Delta Y) \quad (6)$$

As the coordinate reference table, coordinate values expressed as follows are listed:

$$QX'(X, Y) = QX(X, Y) + \Delta X$$
$$QY'(X, Y) = QY(X, Y) + \Delta Y \quad (7)$$

A value with an apostrophe is a corrected value, and a value without an apostrophe is a value not corrected. Moreover, $\Delta X$ or $\Delta Y$ indicates a magnitude of mismatch between an image produced by the master imaging unit and an image produced by the system with the optical adaptor 4 attached thereto.

At step S105, corrected image information data is stored. In other words, the original data calculated at step S104 is stored on a hard disk.

At step S106, image data is acquired. Specifically, an object to be measured is imaged, and the image data thus acquired is stored as raw image data in the memory. At step S107, a subroutine Image Correction (See FIG. 9B) that will be described later is executed in order to correct the raw image data. Specifically, the raw image data acquired at step S106 is subjected to coordinate conversion on the basis of the tables created as original data at step S104. Thus, image data used for measurement is produced.

At step S108, a subroutine Measurement (See FIG. 13) that will be described later is executed on the basis of the image data used for measurement. An arithmetic operation is carried out for calculation of three-dimensional coordinate values, and selected measurement is carried out. The main routine, Stereoscopic Measurement. is then terminated.

Figure 9A:
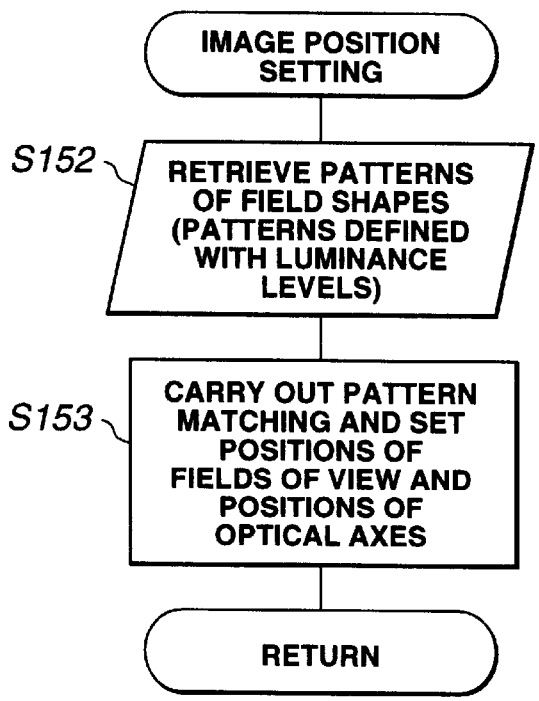
FIG. 9A is a flowchart describing a subroutine Image Position Setting called by the Stereoscopic Measurement method described in FIG. 8.

The subroutine Image Position Setting to be called at step S103 in FIG. 8 will be described in conjunction with the flowchart of FIG. 9A.

Figure 10:
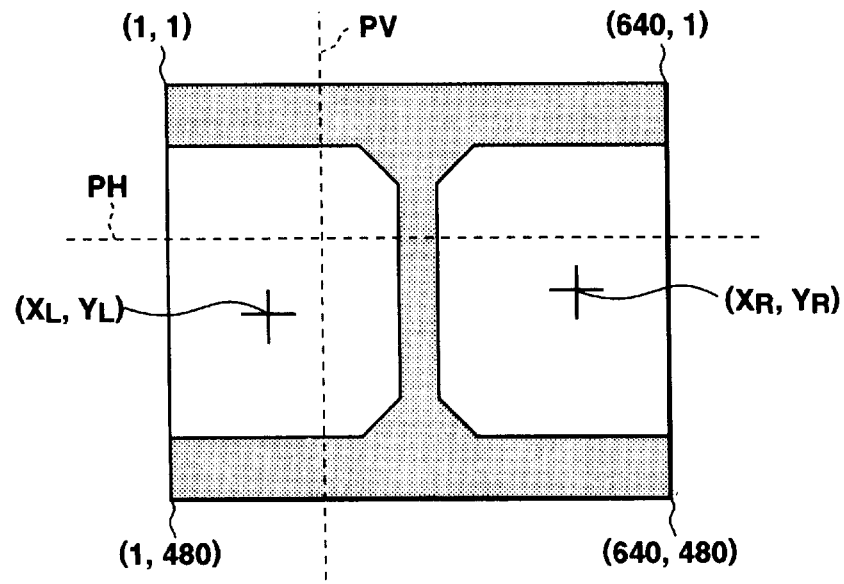
FIG. 10 is a diagram showing images of a white chart produced by attaching an optical adaptor to a master imaging unit included in the measuring endoscope system shown in FIG. 1.

First, at step S152, patterns of field shapes are retrieved. In other words, the data item (d) read at step S101 (luminance data PV(100, Yn) and PH(Xn, 100) where Yn is 1, 2, 3, . . . 480 and Xn is 1, 2, 3, . . . 640 are retrieved as position information based on which the patterns of the shapes of fields of view given by the master imaging unit. FIG. 10 is a diagram showing an image of a white chart produced with the optical adaptor 4 attached to the master imaging unit 34. The vertical line PV and horizontal line PH are lines along which luminance data is acquired.

Figure 11:
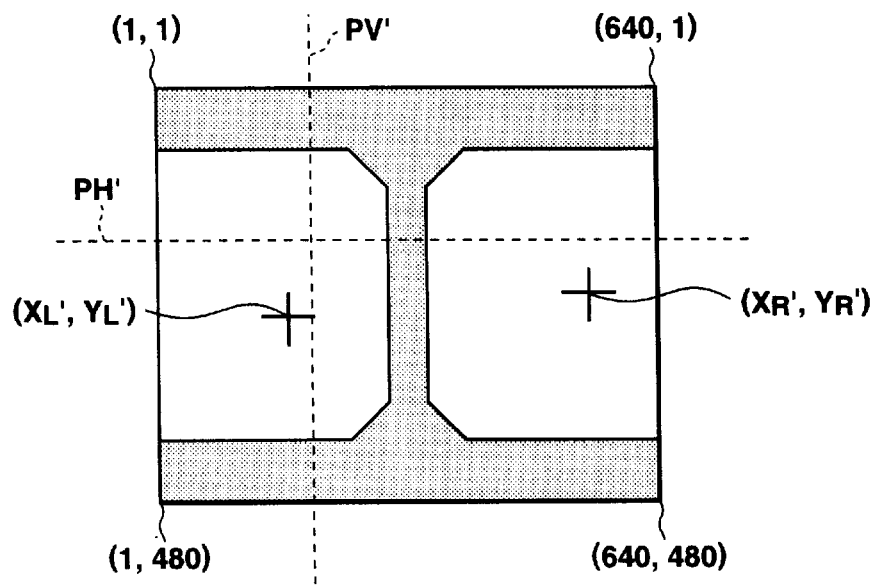
FIG. 11 is a diagram showing images of a white chart produced by attaching the optical adaptor to the endoscope included in the measuring endoscope system shown in FIG. 1.

At step S153, pattern matching, field position setting, and optical-axis position setting are carried out. FIG. 11 is a diagram showing an image of the white chart produced by the measuring endoscope system 1 to which the optical adaptor 4 is attached. Luminance data PV'(100, Yn) and PH'(Xn, 100) where Yn is 1, 2, 3, . . . 480 and Xn is 1, 2, 3, . . . 640 are acquired as position information based on which patterns of field shapes are defined.

Figure 12A:
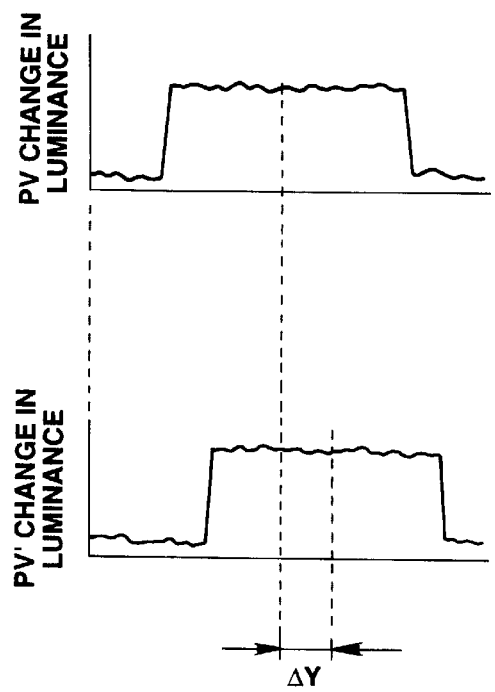
FIG. 12A is a diagram showing waveforms indicating luminance levels which provide patterns of shapes of fields of view given by the measuring endoscope system shown in FIG. 1 and a master imaging unit, or showing changes in luminance data PV and PV' occurring in the vertical direction of images.
Figure 12B:
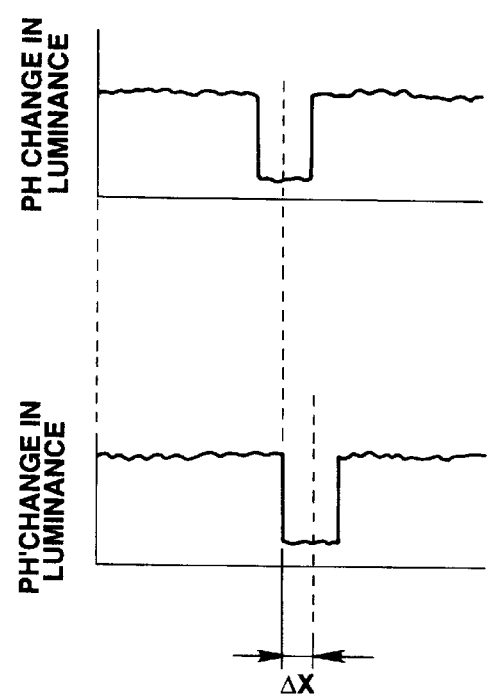
FIG. 12B is a diagram showing waveforms indicating luminance levels which provide patterns of shapes of fields of view given by the measuring endoscope system shown in FIG. 1 and the master imaging unit, or showing changes in luminance data PH and PH' occurring in the horizontal direction of images.

FIGS. 12A and 12B are diagrams each showing changes in luminance by plotting luminance levels versus address of pixel points. These levels define the patterns of the shapes of fields of view given by the master imaging unit and measuring endoscope system 1. FIG. 12A shows changes in luminance along the line PV and line PV', and FIG. 12B shows changes in luminance along the line PH and line PH'.

At step S153 of pattern matching, displacements $\Delta X$ and $\Delta Y$ of an image from a reference image produced by the master imaging unit are calculated by performing normalization correlation on the basis of the luminance changes shown in FIGS. 12A and 12B. The positions of the optical axes of the optical systems, the x coordinates and y coordinates of the right and left optical systems, xR and yR and xL and yL, are calculated as follows:

$$xR = XR + \Delta X$$
$$yR = YR + \Delta Y$$
$$xL = XL + \Delta X$$
$$yL = YL + \Delta Y \quad (8)$$

Figure 9B:
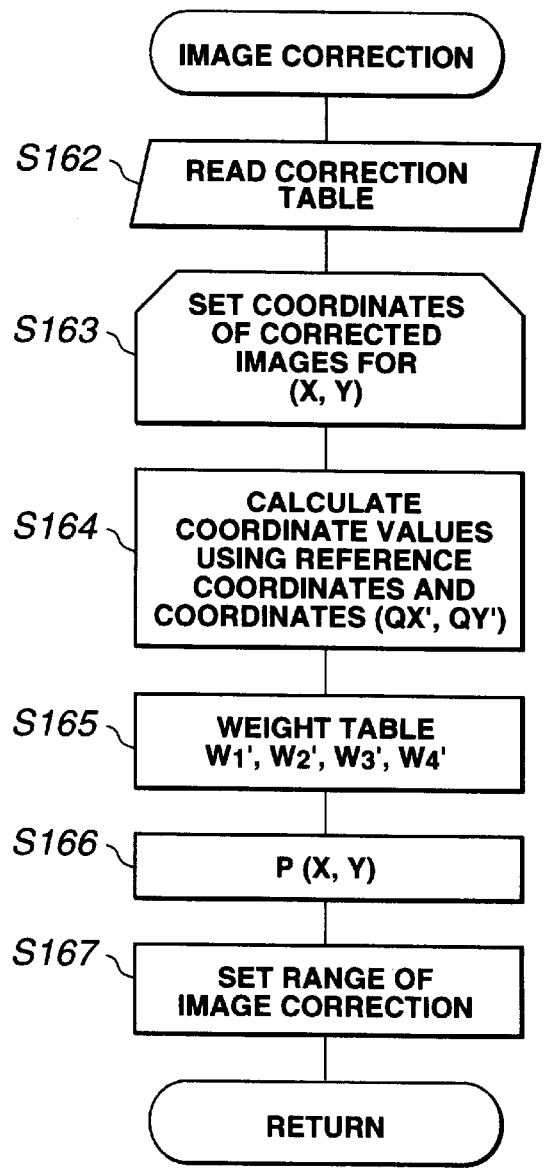
FIG. 9B is a flowchart describing a subroutine Image called by Stereoscopic Measurement method described in FIG. 8.

The subroutine Image Correction called at step S107 (See FIG. 8) will be described in conjunction with the flowchart of FIG. 9B.

The subroutine provides pixel data P(X, Y) with respect to images used for measurement. First, at step S162, the original data is read, (i.e., the correction table created at step S104 (See FIG. 8)). At step S163, the coordinates of corrected images, (i.e., images used for measurement) are set for X and Y.

At step S164, the coordinates of raw images required for calculating the coordinate values X and Y are defined as reference coordinates. The coordinate values X and Y are calculated using the x and y coordinates QX'(X, Y) and QY'(X, Y) calculated at step S104. At step S165, the weight table created at step S104 is read. Pixel data P(X, Y) is calculated using the corrected coordinate values at step S166. That is to say, $$P(X, Y) = p(QX'(X, Y), QY'(X, Y)) \times W1'(X, Y) + \quad (9)$$
$$p(QX'(X, Y) + 1, QY'(X, Y)) \times W2'(X, Y) +$$
$$p(QX'(X, Y), QY'(X, Y) + 1) \times W3'(X, Y) +$$
$$p(QX'(X, Y) + 1, QY'(X, Y) + 1) \times W4'(X, Y)$$

At step S167, a range of image correction is set.

The routine is then terminated. The subroutine Image Correction is performed on two right and left images, whereby raw images are converted into images used for measurement.

Figure 13:
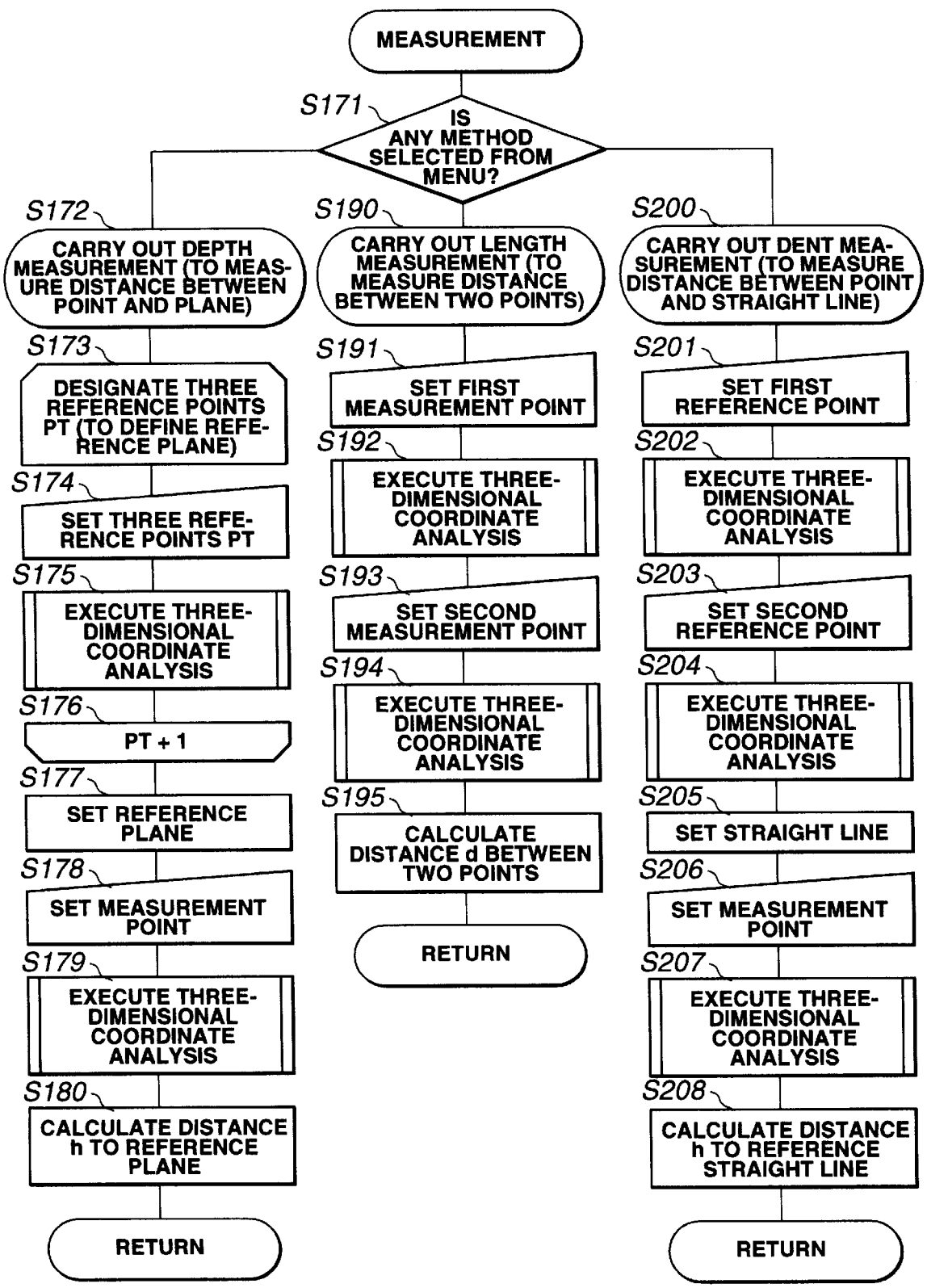
FIG. 13 is a flowchart describing a subroutine Measurement called by the Stereoscopic Measurement method described in FIG. 8.

Next, a subroutine Measurement called at step S108 in FIG. 8 will be described in conjunction with the flowchart of FIG. 13.

First, at step S171, any one of three measuring methods is selected from a menu appearing on the monitor 14. One of the methods is depth measurement. This method is adopted for measuring a distance between a point and plane, for example, as shown in the oblique view of FIG. 15, for measuring a depth h of corrosion occurring in the inner surface of a pipe 51 or the like (See the enlarged view of FIG. 16). When this measuring method is selected, control passes to step S172.

Other method which can be selected at step S171 is length measurement. This method is adopted for measuring a distance between two points, for example, as shown in the oblique view of FIG. 17, for measuring a distance d between two points on the basis of three-dimensional coordinates of the two points on a pipe 52 that is a three-dimensional object to be measured. When this measuring method is selected, control is passed to step S190.

The other method which can be selected at step S171 is dent measurement. This method is adopted for measuring a distance between a point and straight line, for example, as shown in the oblique view of FIG. 18, for measuring a dimension h of a missing part, that is, the size of a missing part of a blade 53 of a turbine. When this measuring method is selected, control passes to step S200.

When depth measurement is selected at step S171 and control is passed to step S172, three reference points PT1, PT2 and PT3, used to define a reference plane, are set at steps S173 to S175. For example, reference points PT1, PT2, and PT3 on the pipe 51 in FIG. 15 are specified. The three-dimensional coordinates of the three points are then obtained by executing a subroutine Three-dimensional Coordinate Analysis that will be described later (See FIG. 14A).

Figure 15:
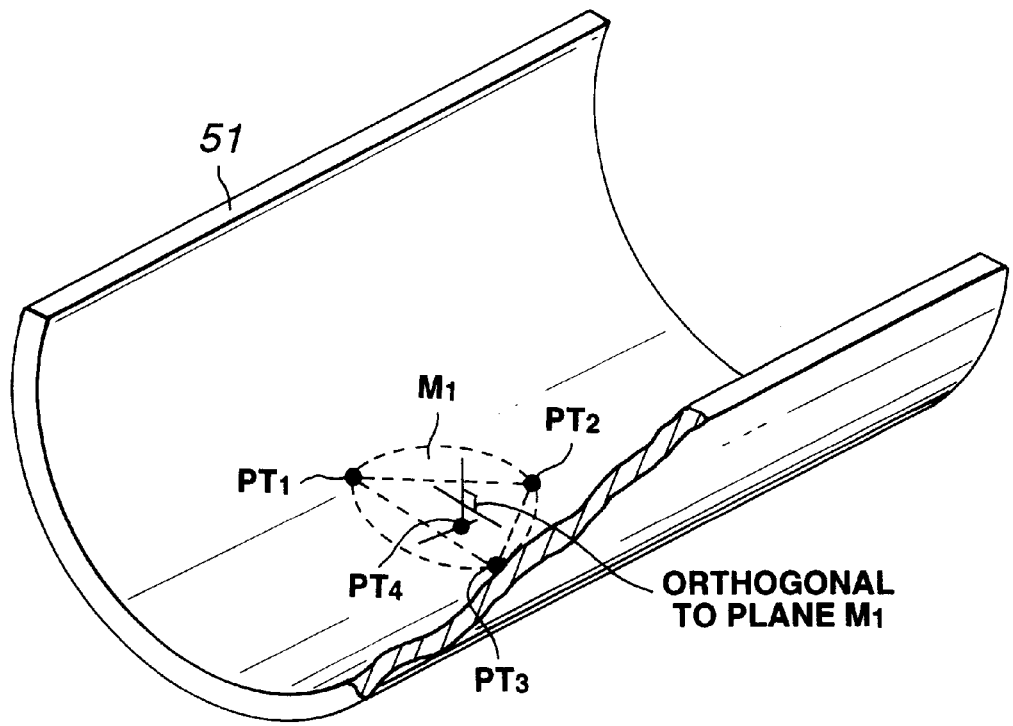
FIG. 15 is an oblique view showing a state in which the measuring endoscope system shown in FIG. 1 is used to measure a depth in a pipe.
Figure 16:
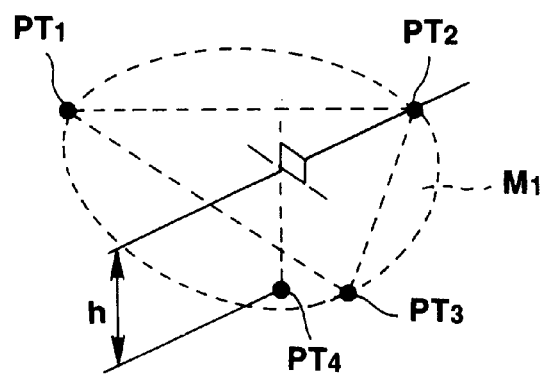
FIG. 16 is an enlarged view of a measured portion of the pipe shown in FIG. 15.

At step S176, a point (PT) indicator is incremented. At step S177, a plane defined by the three points is set as a reference plane. In the case of FIG. 15, a plane M1 containing the points PT1, PT2, and PT3 is set. At step S178, a measurement point, for example, a point PT4 is specified. At step S179, the subroutine Three-dimensional Coordinate Analysis (See FIG. 14A) is called and executed in order to calculate the coordinate values of the measurement point. In the case of FIG. 16, the coordinate values of the point PT4 are calculated.

At step S180, a distance from the reference plane to the measurement point is calculated. In the case of FIG. 16, the distance h from the measurement point PT4 to the reference plane M1 which gives the depth of a corrosion is calculated. The routine is then terminated.

When length measurement is selected at step S171, control is passed to step S190. A first measurement point is set at step S191. At step 192, the subroutine Three-dimensional Coordinate Analysis (FIG. 14A) is executed in order to calculate coordinate values defining the first measurement point. At step S193, a second measurement point is set. At step S194, the subroutine Three-dimensional Coordinate Analysis is executed in order to calculate coordinate values defining the second measurement point. Thereafter, at step S195, a distance d between the two points of the first and second measurement points is calculated on the basis of the coordinates of the first and second measurement points. The subroutine is then terminated.

Figure 17:
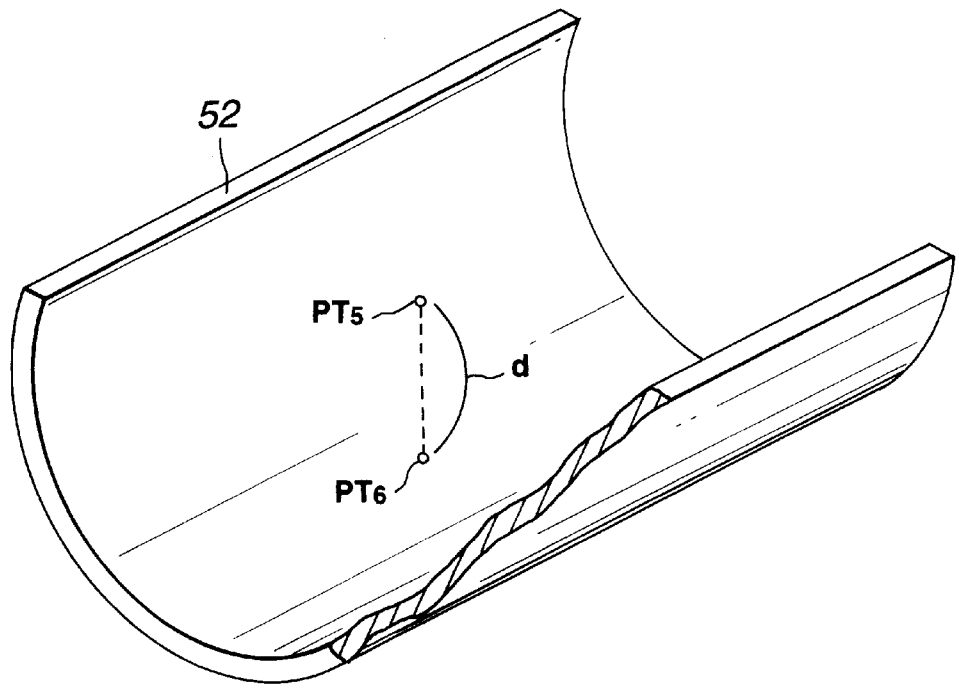
FIG. 17 is an oblique view showing a state in which the measuring endoscope system shown in FIG. 1 is used to measure a length in a pipe.

With respect to the foregoing processing, assuming that an object to be measured is the pipe 52 shown in FIG. 17, and the first and second measurement points are points PT5 and PT6, the distance d between the two points is calculated by carrying out the foregoing measurement.

When dent measurement is selected at step S171, control passes to step S200. At step S201, a first reference point is set at one edge of a dent. At step S202, the subroutine Three-dimensional Coordinate Analysis (FIG. 14A) is executed in order to calculate coordinate values defining the first reference point. At step S203, a second reference point is set at another edge of the dent. At step S204, the subroutine Three-dimensional Coordinate Analysis is executed in order to calculate coordinate values defining the second reference point. At step S205, a reference straight line linking the two points is set on the basis of the coordinates of the first and second reference points.

At step S206, a dent measurement point is set. At step S207, the subroutine Three-dimensional Coordinate Analysis is executed in order to calculate coordinate values defining the measurement point. At step S208, the length, h, of a perpendicular extending from the measurement point to a straight line linking the reference points is calculated as a magnitude of dent. The routine is then terminated.

Figure 18:
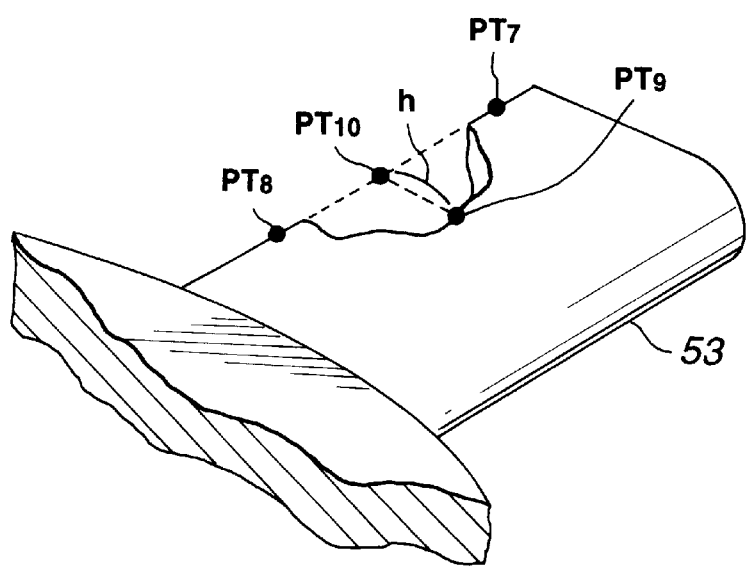
FIG. 18 is an oblique view showing a state in which the measuring endoscope system shown in FIG. 1 is used to measure a dent in a blade of a turbine.

When an object to be measured by executing the subroutine is a blade of a turbine shown in FIG. 18, the distance, h, from a reference straight line linking the first and second reference points PT7 and PT8 to the dent measurement point PT9 is calculated.

Figure 14A:
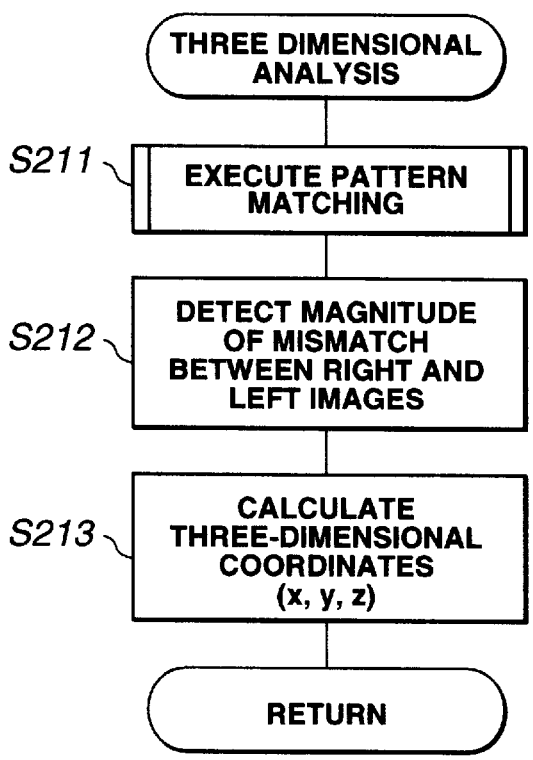
FIG. 14A is a flowchart describing a subroutine Three-dimensional Coordinate Analysis called by the Measurement method described in FIG. 13.

FIG. 14A illustrates the subroutine Three-dimensional Coordinate Analysis called at the previously described steps S175, S192, S202, or any other step.

Figure 14B:
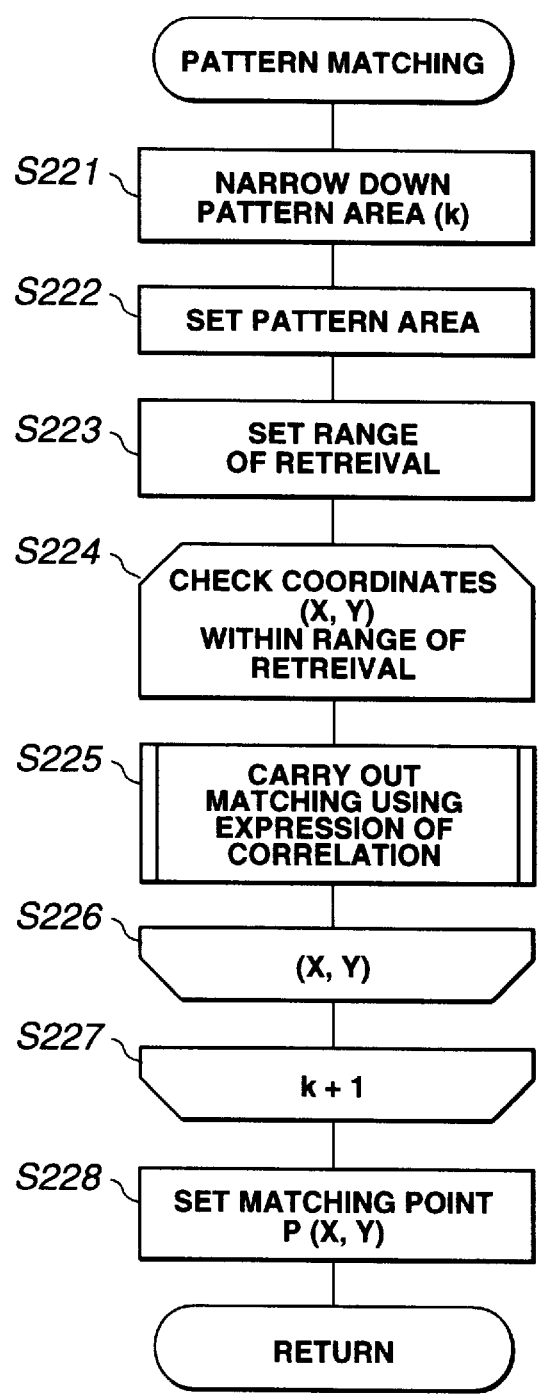
FIG. 14B is a flowchart describing a subroutine Pattern Matching called by the Measurement method described in FIG. 13.

At step S211, a subroutine Pattern Matching is executed (see FIG. 14B). Matching points that are corresponding points in right and left images (images realizing stereoscopy) are detected. At step S212, a magnitude of mismatch between the right and left images is calculated on the basis of the coordinates of the corresponding points. At step S213, the three-dimensional coordinates of a point concerned are calculated. The routine is then terminated.

The principles of three-dimensional coordinate analysis carried out as the subroutine will be described in conjunction with FIG. 19.

Figure 19:
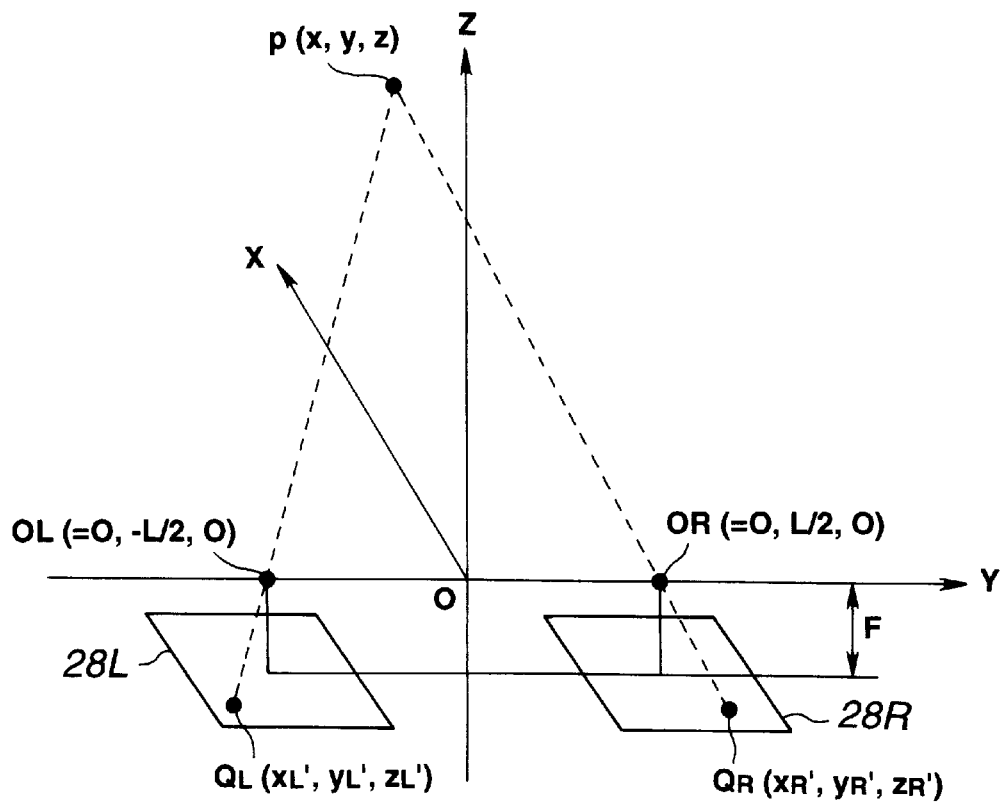
FIG. 19 is a diagram explaining the principles of three-dimensional coordinate analysis performed by the measuring endoscope system shown in FIG. 1, and showing the positional relationship between the two right and left images developed in the system of three-dimensional coordinates having x, y, and z axes.

FIG. 19 is a diagram showing the positional relationship between two right and left images in the system of three-dimensional coordinates having x, y, and z axes. An image of a point P of an object is formed on a right image formation surface 28R and left image formation surface 28L of the imaging device 28. In the drawing, assume that points OR and OL are positions of entrance pupils of optical systems, a distance f is a focal length, points QR and QL are positions at which the images of the point P are formed, and a distance L is a distance between the point OR and point OL.

When a straight line QR-OR is defined using the coordinates specified in the drawing, the expression below can be drawn out.

$$x/xR' = \{y - (L/2)\}/\{yR' - (L/2)\} = z/(-f) \quad (10)$$

When a straight line QL-OL is defined using the coordinates specified in the drawing, the expression below can be drawn out.

$$x/XL' = \{y + (L/2)\}/\{yL' + (L/2)\} = z/(-f) \quad (11)$$

The solution of x, y, and z satisfying the above expressions provides the three-dimensional coordinates of the point P.

The subroutine Pattern Matching which is called at step S211 within Three-dimensional Coordinate Analysis described in FIG. 14A will be described in conjunction with the flowchart of FIG. 14B.

Figure 20:
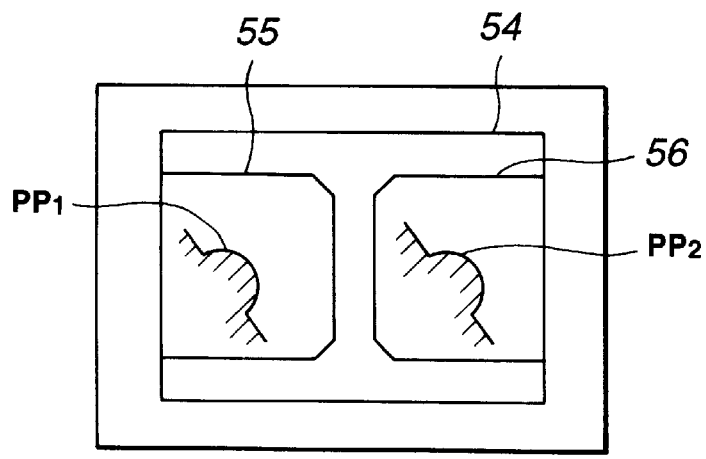
FIG. 20 is a diagram showing a stereoscopic measurement screen, in which the two right and left images are displayed, on a monitor included in the measuring endoscope system shown in FIG. 1.

This routine carries out pattern matching for detecting corresponding points in two images. FIG. 20 shows a stereoscopic measurement screen 54 on the monitor 14 in which right and left images 55 and 56 are displayed. An image point PP1 in the left image 55 corresponds to an image point PP2 in the right image 56.

First, at steps S221 and 222, a pattern area is narrowed down in order to set the size of patterns to be matched. In the example according to this embodiment, the pattern area is set according to a value k. That is to say;

when k=1, the pattern area has the size of 36 by 36 (pixels);

when k=2, the pattern area has the size of 24 by 24 (pixels); and when k=3, the pattern area has the size of 12 by 12 (pixels).

The value k is made larger in order to narrow down the area. This leads to higher precision in detecting corresponding points.

At step S223, a range of retrieval is set.

Specifically, an area in the right image in which a pattern is searched for is determined. For setting the range of retrieval, the range may be defined on an epi-polar line with a tolerance of ±5 pixels or with a tolerance of ±7 pixels horizontally in a monitor screen in consideration of an error, or may be defined with a nearly matching point, which is manually designated in the screen, as a center with a tolerance of ±10 pixels. ±10 pixels is an optimal value in consideration of an error occurring by manual matching.

At steps S224 to S226, pattern matching is carried out within the designated range of retrieval. For the pattern matching, a corresponding point is detected by carrying out normalization correlation. A point defined with coordinates (X, Y) offering the largest coefficient of normalization correlation is adopted as the corresponding point.

At step S227, the value k is incremented. The pattern searched for is narrowed down according to the value k, and then a corresponding point is detected. At step S228, a matching point is set. At this time, the coefficient of normalization correlation may be displayed in a monitor screen and used as an index of reliability of matching. If the coefficient of normalization correlation (0 to 1) is smaller than a given value, the matching mode may be switched to manual matching.

An expression of normalization correlation employed in the pattern matching, M(u,v), is typically as follows:

$$M(u, v) = \left\{ \sum_S \sum (f(x+u, y+v) - f')(t(x, y) - t') \right\} / \left\{ \sqrt{\sum_S \sum (f(x+u, y+v) - f'^2) \times \sum \sum (t(x, y) - t')^2} \right\} \quad (12)$$

where t(x, y) gives a template, f(x, y) gives image data, t' denotes an average luminance level of the template, and f' is an average luminance level of an image.

For brevity's sake, processing of image data according to the embodiment has been described by taking a monochrome image for instance. Needless to say, the processing may be adapted to a color image realized with red, green, and blue signals and would still prove effective.

As mentioned above, according to the measuring endoscope system 1 of this embodiment, optical data specific to the optical adaptor 4 is provided in the form of the FD 33 that is a recording medium, and a difference in coordinates between images produced by the production jig 39 (master imaging unit 34 of FIG. 5) and endoscope is corrected. Consequently, measurement precision can be improved.

The production jig 39 (master imaging unit 34) is used to acquire optical data specific to the optical adaptor 4 designed for measurement in the course of manufacturing. This results in improved productivity. Consequently, the measuring endoscope system 1 can be provided at a low price.

The optical adaptor 4 used for measurement is freely attachable or detachable to or from the distal endoscope part 5, and can therefore be exchanged for an optical adaptor other than the optical adaptor designed for measurement. For example, when a direct-view type or oblique-view type optical adaptor serving as a single-lens optical adaptor or an optical adaptor having a different angle of view can be attached, the range of diverse usages of an endoscope can be expanded. As a consequence, a financial burden incurred by a user by having several different endoscopes, each for a different purpose can be caused.

In this embodiment, the weight table containing the weights W1 to W4 (used to perform coordinate conversion on images) and the coordinate reference table listing coordinate values QX and QY are both created by the computer 36 and then recorded on the FD 33. This obviates the necessity of creating the tables by means of a computer incorporated in the measuring apparatus 3. Measurement therefore requires only a short period of time.

The coefficient of normalization correlation is displayed in a screen on the monitor 14. This informs an operator of the reliability of matching or measurement. Moreover, if the coefficient of normalization correlation is small, the matching mode can be switched to manual matching. This results in highly accurate measurements.

Figure 32A:
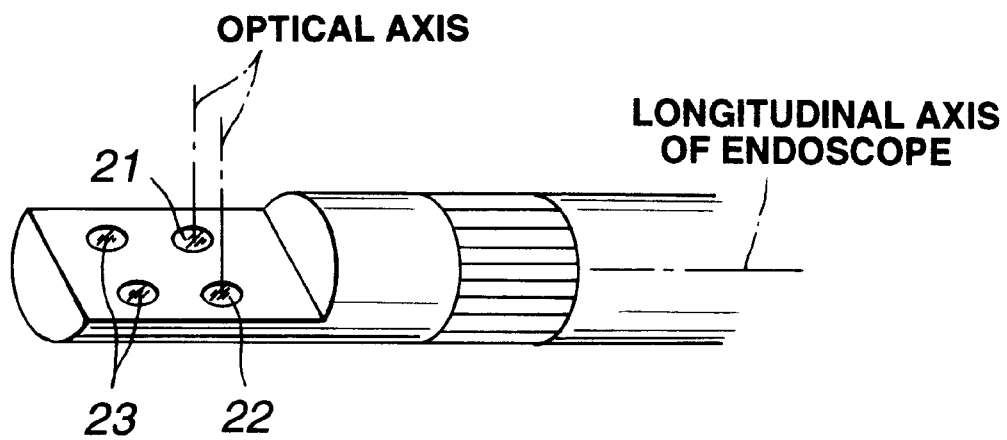
FIG. 32A is a diagram showing an endoscope including an optical adaptor whose two objective lenses are oriented in such a manner that the optical axes thereof are orthogonal to the longitudinal axis of the endoscope.
Figure 32B:
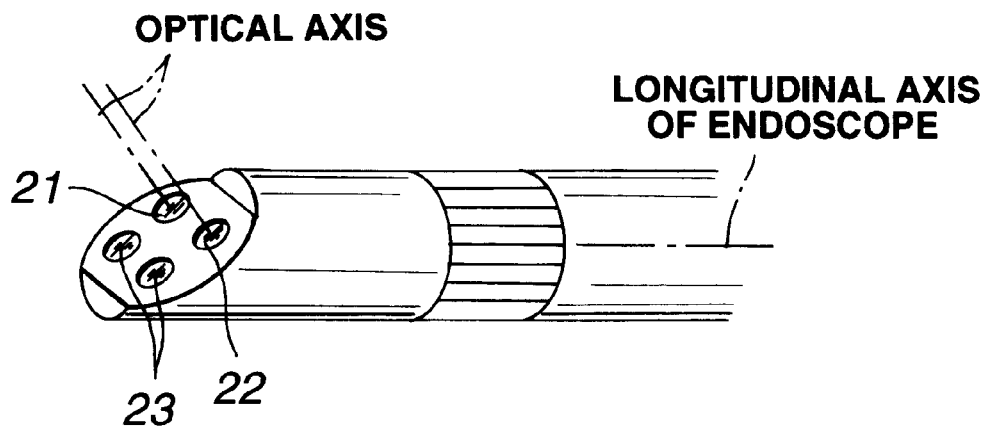
FIG. 32B is a diagram showing an endoscope including an optical adaptor whose two objective lenses are oriented in such a manner that the optical axes thereof are tilting with respect to the longitudinal axis of the endoscope.

The f numbers rating the two objective lenses 21 and 22 of the optical adaptor 4 may be substantially identical or different from each other. When the f numbers rating the two objective lenses 21 and 22 are different, for example if one of the lenses is a wide-angle lens and the other lens is a narrow-angle lens, both an image taken in a wide field of view and an enlarged image can be produced. Accordingly, efficiency in endoscopic inspection improves. As shown in FIG. 4, the optical axes of the objective lenses 21 and 22 in the optical adaptor may be substantially parallel to the longitudinal axis of the endoscope. As shown in FIGS. 32A and 32B, the optical axes of the objective lenses 21 and 22 may be orthogonal or oblique to the longitudinal axis of the endoscope.

Next, a measuring endoscope system in accordance with the second embodiment of the present invention will be described.

The measuring endoscope system in accordance with the second embodiment has the same system configuration as the one in accordance with the first embodiment but is different therefrom in a measurement control method. The same reference numerals will be assigned to the same components.

In the measuring endoscope system of this embodiment, among optical data items specific to the optical adaptor 4 which is recorded in the FD 33 that is a recording medium, the geometric distortion correction table alone requires different parameters. That is to say, (a') The coefficients $a_{nm}$ and $b_{nm}$ in the expressions (1) and (2) are used as parameters of the geometric distortion correction table.

(b) The focal length fR from the right system of lenses for acquiring a right image and the focal length fL from the left system of lenses for acquiring a left image are, like those in the first embodiment, recorded as the focal lengths from two systems of lenses.

(c) The coordinates XR and YR of the optical axis of the system of lenses for acquiring a right image, and the coordinates XL and YL of the optical axis of the system of lenses for acquiring a left image are, like those in the first embodiment, measured and recorded as the coordinates of the optical axes of the two systems of lenses.

(d) Luminance data detected along the reference line V, PV(100, Yn) where Yn is 1, 2, 3, . . . 480, and luminance data detected along the reference line H, PH(Xn, 100) wherein Xn is 1, 2, 3, . . . 640, are, like those in the first embodiment, measured and recorded as position information of two images relative to the master imaging unit (patterns of field shapes).

Figure 21:
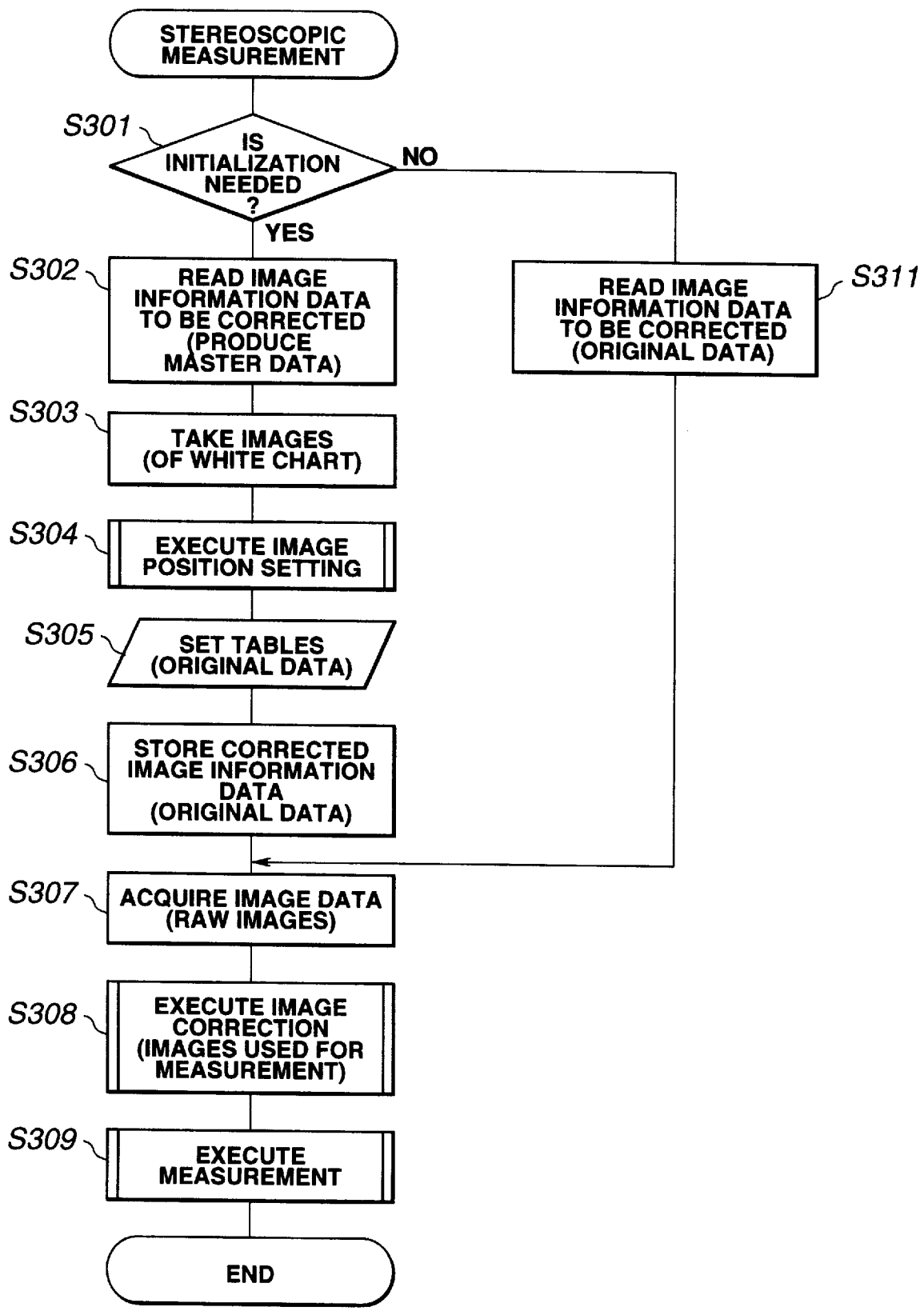
FIG. 21 is a flowchart describing a stereoscopic measurement method performed by a measuring endoscope system in accordance with the second embodiment of the present invention.

FIG. 21 is a flowchart describing stereoscopic measurement carried out by the measuring endoscope system of the second embodiment. The stereoscopic measurement is identical to the contents of the routine employed in the first embodiment described in FIG. 8 except with respect to the processing of steps S302 and S309.

For reading image information data to be corrected at step S302, master data is created by acquiring the foregoing optical data items (a'), (b), (c), and (d) using the computer 18 incorporated in the measuring apparatus 3.

Figure 22:
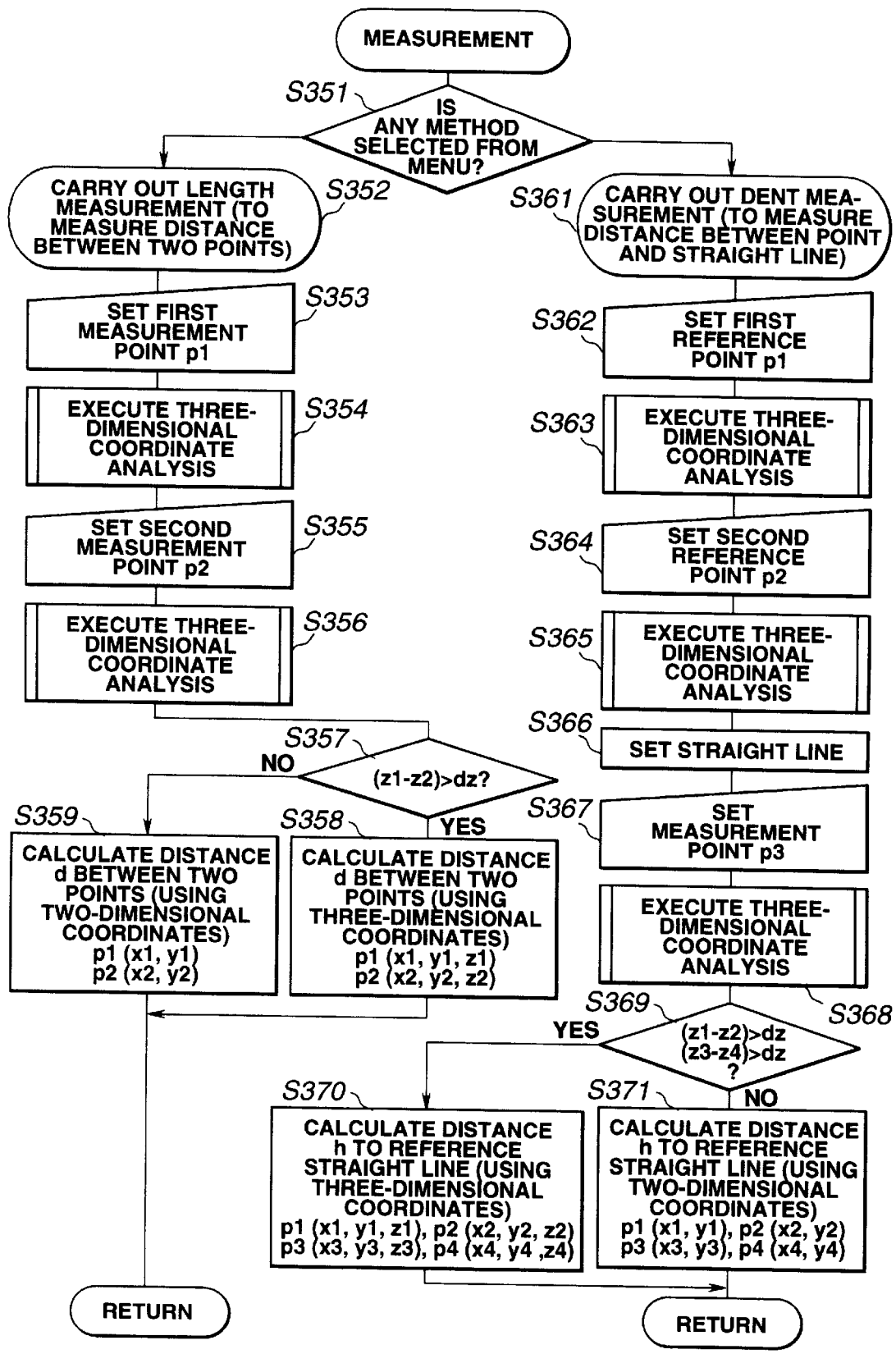
FIG. 22 is a flowchart describing a subroutine Measurement called by the Stereoscopic Measurement method described in FIG. 21.

A subroutine Measurement, called at step S309, is described in the flowchart of FIG. 22. The processing of steps S352 to S356 that is length measurement and the processing of steps S361 to S368 that is dent measurement, are identical to the processing of steps S190 to S194 and the processing of steps S200 to S207 which are carried out within the subroutine Measurement in accordance with the first embodiment described in FIG. 13. However, the processing succeeding step S356 and the one succeeding step S368 are different.

Specifically, at step S357 during length measurement, a difference between a z coordinate value z1 of a first measurement point p1 and a z coordinate value z2 of a second measurement point p2 is calculated. If the difference exceeds a given value dz, the processing of step S358 is carried out. Otherwise, the processing of step S359 is carried out.

The processing of step S358 is calculation of three-dimensional coordinate values, while the processing of step S359 is calculation of two-dimensional coordinate values. For calculating a distance between the two points of the first measurement point p1 and second measurement point p2, the distance is calculated in the system of two-dimensional coordinates having x and y axes.

The reason why a different type of processing is executed depending on whether the difference between z coordinate values is larger or smaller is because a measurement error of a z coordinate value providing depth information is more critical than a measurement error of an x or y coordinate value out of three-dimensional coordinate values employed in stereoscopic measurement requiring two right and left images. When the difference dz in z coordinate value between the first measurement point p1 and second measurement point p2 is smaller than the given value, the distance between the two points should be calculated using only the x and y coordinate values because an error is smaller. This leads to higher-precision measurement.

At step S369 during dent measurement processing, a difference between z coordinate values of points is calculated. Assuming that the z coordinate values of the first reference point P1 and second reference point P2 are z1 and z2, and the z coordinate values of the measurement point P3 and an intersection P4 orthogonal to the reference straight line extending from the measurement point are z3 and z4, differences (z1–z2) and (z3–z4) are compared with the given value dz. If both the differences are larger, control is passed to step S370 and calculation is carried out using three-dimensional coordinate values. If both the differences are not larger, control is passed to step S371 and calculation is carried out using two-dimensional coordinate values. Owing to this processing, for the same reason as previously described, dent measurement can be carried out with higher precision.

Next, a monitor display method will be described which is used when the measuring endoscope system in accordance with the first embodiment or second embodiment carries out measurement.

Figure 23A:
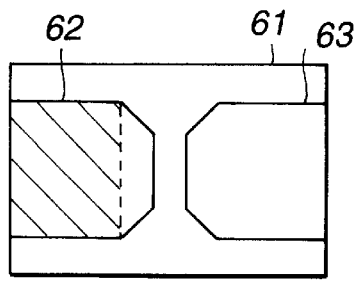
FIG. 23A is a diagram showing a display screen on a liquid-crystal monitor according to an example of a display method for the measuring endoscope system shown in FIG. 1, and showing a state in which two right and left images are displayed.
Figure 23B:
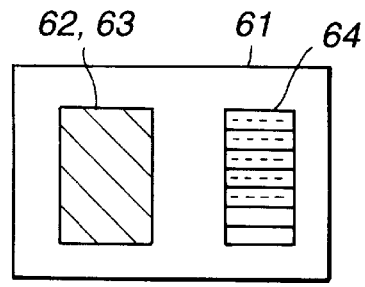
FIG. 23B is a diagram showing a display screen on the liquid-crystal monitor according to an example of a display method for the measuring endoscope system shown in FIG. 1, and showing a state in which a right or left image and a processing menu are displayed.

FIGS. 23A and 23B show examples of a display screen 61 on the liquid-crystal monitor 14. FIG. 23A shows a state in which right and left images 63 and 62 produced by the endoscope are displayed, and FIG. 23B shows an example of displaying the right or left image and a menu 64.

When either of the right image 63 and left image 62 is selected and displayed on the left side of the screen 61 on the liquid-crystal monitor 14, if a menu 64 is displayed on the right side thereof, any item can be selected from the menu 64 on the right side while reference is made to the image on the left side. This facilitates selection of an item.

Figure 24A:
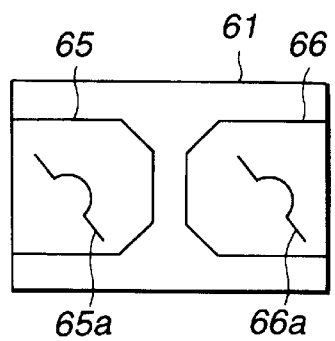
FIG. 24A is a diagram showing a monitor screen displaying right and left images that are edge images extracted from taken images according to another example of a display method for the measuring endoscope system shown in FIG. 1, and showing a state in which the two right and left images are displayed.
Figure 24B:
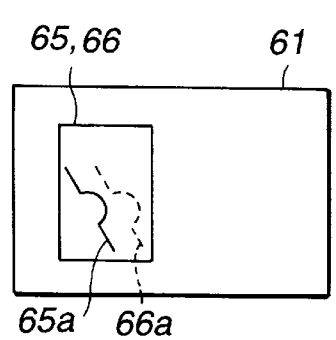
FIG. 24B is a diagram showing a monitor screen displaying the right and left images that are the edge images extracted from the taken images according to another example of a display method for the measuring endoscope system shown in FIG. 1, and showing a state in which the right and left images are superposed on each other.

FIG. 24A shows an example of the screen 61 on the liquid-crystal monitor 14 in which a right image 66 and left image 65 produced by the endoscope are displayed. Extracted edges 65a and 66a are shown in left 65 and right 66 images respectively. FIG. 24B shows an example in which the left image 65 is displayed and the edge 66a is superposed on the left image 65. For detecting a corresponding point by matching images realizing stereoscopy, when one of the images showing edges is moved by manipulating a cursor or the like and superposed on the other image, the corresponding point can be easily detected.

Figure 25A:
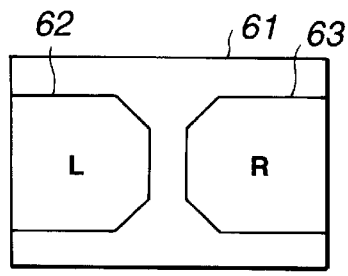
FIG. 25A is a diagram showing an example of displaying right and left images in a screen on a liquid-crystal monitor according to yet another example of a display method for the measuring endoscope system shown in FIG. 1, and showing a state in which the right and left images are displayed on the right and left sides of the screen.
Figure 25B:
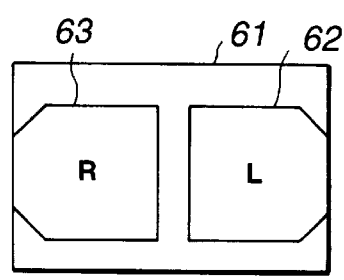
FIG. 25B is a diagram showing an example of displaying right and left images in a screen on the liquid-crystal monitor according to yet another example of a display method for the measuring endoscope system shown in FIG. 1, and showing a state in which the right and left images are switched.

FIGS. 25A and 25B show examples of displaying right and left images 63 and 62 in the screen 61 on the liquid-crystal monitor 14. FIG. 25A shows a state in which the right and left images 63 and 62 are displayed, respectively, on the right side and left side of the screen 61. FIG. 25B shows a state in which the right and left images R63 and L62 are switched and displayed on opposite portions of screen 61.

When an imaging device is used to take images realizing stereoscopy, a right image can be displayed on the left side of the liquid-crystal monitor 14, and a left image can be displayed on the right side thereof. This may cause an operator to make a misjudgment. However, as shown in FIG. 25A, the left image 62 can be displayed on the left side of the liquid-crystal monitor and the right image 63 can be displayed on the right side thereof. Owing to this display format, images can be displayed in the same manner as they are seen by human eyes. Consequently, a misjudgment likely to be made during measurement can be prevented.

Figure 26A:
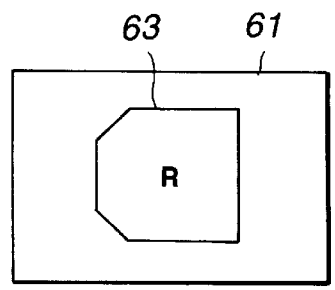
FIG. 26A is a diagram showing an example of displaying right and left images on the liquid-crystal monitor by performing interlacing according to still another example of a display method for the measuring endoscope system shown in FIG. 1, and showing a state in which the right image is displayed as even-numbered lines of interlacing lines constituting a TV picture.
Figure 26B:
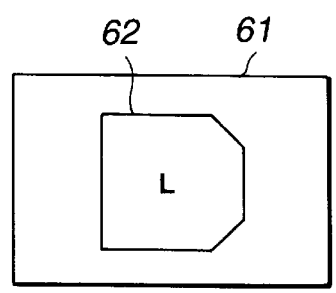
FIG. 26B is a diagram showing an example of displaying right and left images on the liquid-crystal monitor by performing interlacing according to still another example of a display method for the measuring endoscope system shown in FIG. 1, and showing a state in which the left image is displayed as odd-numbered lines of interlacing lines constituting a TV picture.

FIGS. 26A and 26B show examples of interlacing of right and left images on the liquid-crystal monitor 14. In the examples of images displayed on the monitor, a right image 63 is, as shown in FIG. 26A, displayed as even-numbered lines out of interlacing lines constituting a TV picture, and a left image L62 is, as shown in FIG. 26B, displayed as odd-numbered lines out of the interlacing lines constituting the picture. Spectacles having liquid-crystal shutters interlocked with the interlacing are used to view the images shown in FIGS. 26A and 26B, whereby stereoscopy is achieved. The positions of the right and left images are adjusted so that stereoscopy can be achieved, and then the right 63 and left 62 images are displayed. According to this embodiment, an operator can observe an object to be measured while faithfully visualizing the object.

Next, a measuring endoscope system in accordance with the third embodiment of the present invention will be described.

The measuring endoscope system is different from the one in accordance with the first embodiment with respect to the method of calculating data items listed in geometric distortion correction table. The other components of the system of the third embodiment are identical to those of the system in accordance with the first embodiment. The same reference numerals are assigned to the same components. The description of the components will be omitted.

In the system of this embodiment, optical data specific to an optical adaptor is acquired by the production jig 39 shown in FIG. 4, and recorded on the FD 33 that is a recording medium. The information below is recorded as part of the optical data. That is to say, the same data as the data employed in the first embodiment is recorded in the form of (a") a geometric distortion correction table which is used to correct geometric distortions in two images. Data items below are recorded in the form of the weight table.

W1(X, Y)
W2(X, Y)
W3(X, Y)
W4(X, Y)

Data items below are recorded in the form of the coordinate reference table.

QX(X, Y), QY(X, Y)

Arithmetic operations for calculating the data items in this embodiment are different as described below.

Figure 27:
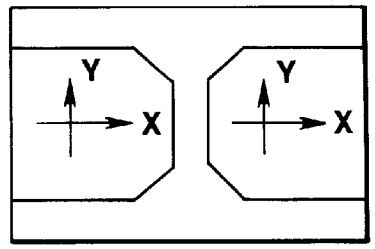
FIG. 27 is a diagram showing systems of coordinates used to create a geometric distortion correction table in a measuring endoscope system in accordance with the third embodiment of the present invention.
Figure 28:
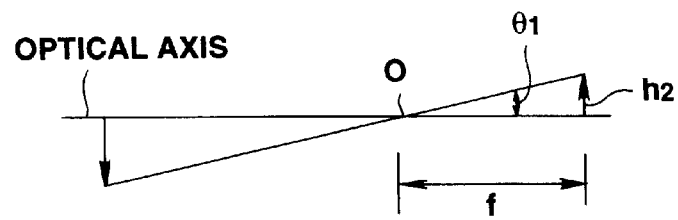
FIG. 28 is a diagram showing the principles of an optical system concerning an image height required for creating the geometric distortion correction table in the measuring endoscope system shown in FIG. 27.
Figure 29:
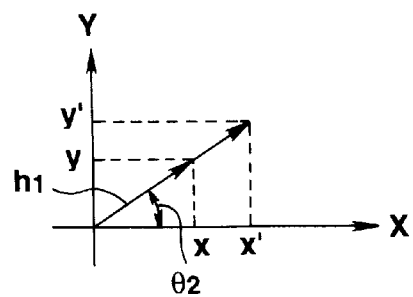
FIG. 29 is a diagram showing coordinate conversion performed on image data for creating the geometric distortion correction table in the measuring endoscope system shown in FIG. 27.

In general, an image taken by a system of lenses suffers from an optical distortion. This distortion causes a critical error in measurement. The distortion is therefore canceled by carrying out coordinate conversion. Referring to FIGS. 6 and 7, FIG. 27 shows a system of coordinates used to create a geometric distortion correction table, FIG. 28 illustrates the principles of an optical system and the height of an image, and FIG. 29 illustrates coordinate conversion of image data. How a correction table is created in accordance with this embodiment will be described.

Points p1 to p4 (FIGS. 6 and 7) indicate pixels not having undergone coordinate conversion. When coordinate conversion is performed on the points p1 to p4 by expressing them as functions of x and y coordinates in the form of f(x, y), the points p1 to p4 are converted to points p1' to p4'. The coordinate values defining the points p1' to p4' are real numbers.

In order to display images on a liquid-crystal monitor, the image data must be converted into pixel data P(X, Y) dependent on coordinate values of integers. The conversion is carried out using the weights W1 to W4 listed in the weight table. The coordinate conversion of this third embodiment is identical to that employed in the first embodiment. This embodiment is different from the first embodiment in a point that the function f(x, y) is expanded using the equations below. That is to say, $$h1 = \sqrt{x^2 + y^2} \tag{13}$$

$$\theta1 = Ks \times \sin^{-1}(h1/(f \times Ks)) \tag{14}$$

$$\theta1 = Kt \times \tan^{-1}(h1/(f \times Kt)) \tag{15}$$

$$h2 = f \times \tan\theta1 \tag{16}$$

$$\theta2 = \tan^{-1}(y/x) \tag{17}$$

$$x' = h2 \times \cos(\theta2) \times k1 \tag{18}$$

$$y' = h2 \times \sin(\theta2) \times k2 \tag{19}$$

The expressions (14) and (15) are selectively used according to a geometric distortion characteristic of an objective lens. The values Ks and Kt are modified according to the degrees of the geometric distortions caused by objective lenses. f denotes a focal length. k1 and k2 are coefficients used to match magnifications of two images and functions of the focal lengths fR and fL respectively.

The coordinates of the points p1 to p4, (x, y) to (x+1, y+1) are assigned to the expressions (13) to (17). The solutions of the expressions are input to the expressions (18) and (19), thus calculating the coordinates (x', y') to (x'+1, y'+1) of the points p1'(x', y') to p4'(x'+1, y'+1). Based on the coordinate data, the x and y coordinate values QX(X, Y) and QY(X, Y) of the coordinate reference table are calculated.

A system of coordinates to be employed in this embodiment is not limited to the aforesaid one. Various systems of coordinates can be utilized if necessary.

Furthermore, pixel data P(X, Y) resulting from coordinate conversion may be calculated using the coordinate data of the points p1' to p4' and the weights W1 to W4 in the same manner as that in the first embodiment.

Assuming that dn denotes a distance from the point p1', p2', p3', or p4' to the point P(X, Y), the following relationship is established:

$$S = d1 + d2 + d3 + d4$$

The weights W1 to W4 are expressed as follows:

$$W1 = d1/S$$
$$W2 = d2/S$$
$$W3 = d3/S$$
$$W4 = d4/S$$

Consequently, $$P(X,Y) = W1 \times p1' + W2 \times p2' + W3 \times p3' + W4 \times p4'$$

The weight table having the weights W1, W2, W3, and W4 listed therein, and the coordinate reference table having the coordinate values QX(X, Y) and QY(X, Y), which give x and y coordinates of a point in a raw image required for calculating the pixel data P(X, Y), listed therein are recorded as a geometric distortion correction table on the FD 33.

The other specific optical data items are described below.

(b) A focal length fR from a right system of lenses for acquiring a right image and a focal length fL from a left system of lenses for acquiring a left image are, like those in the first embodiment, recorded as the focal lengths of the two systems of lenses.

(c) The coordinates XR and YR of the optical axis of the right system of lenses for acquiring the right image, and the coordinates XL and YL of the optical axis of the left system of lenses for acquiring the left image are, like those in the first embodiment, measured and recorded as the coordinates of the optical axes of the two systems of lenses.

(d) Luminance data detected along a reference line V, PV(100, Yn) where Yn is 1, 2, 3, . . . 480, and luminance data detected along a reference line H, PH(Xn, 100) where Xn is 1, 2, 3, . . . 640 are, like those in the first embodiment, measured and recorded as position information of two images relative to the master imaging unit (patterns of field shapes).

In the first to third embodiments, optical data specific to an optical adaptor may not include data of focal lengths from two systems of lenses which can be measured with a relatively little error. Nevertheless, measurement can be achieved in a more satisfactory manner than that in accordance with the prior art.

The monitor display method described in conjunction with FIGS. 23A to 26B can be adapted to be carried out during measurement performed by the measuring endoscope system of this embodiment.

Next, an inspection system for inspecting blades of a jet engine will be described as a measuring endoscope system in accordance with a practical embodiment of the present invention.

Known inspection of blades of a turbine is such that while an endoscopic image is observed, the blades are turned using a turning tool, for example, a motor-driven jig for turning the shaft of the turbine; and when a given position of the turbine is detected, an operator stops the tuning tool and carries out measurement. However, the number of blades included in such a turbine is several hundred. The turbine is stopped for every inspection of a blade. The workability is therefore very poor. An inspection system employing the measurement system of the present invention can overcome such a drawback and offer excellent workability.

Figure 30:
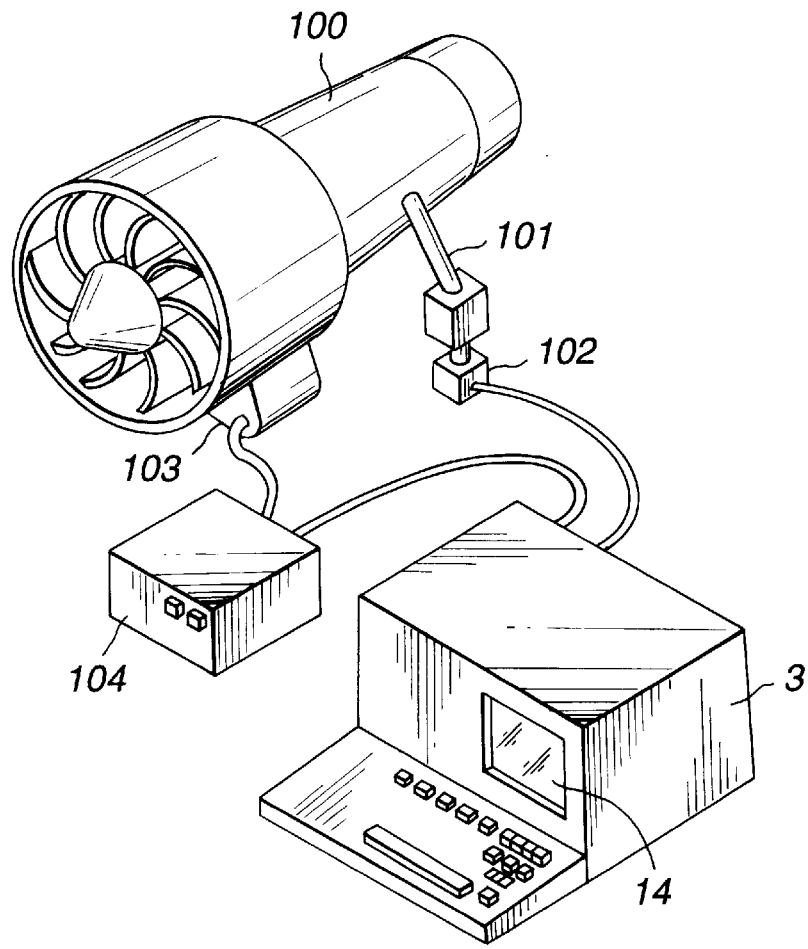
FIG. 30 is a diagram showing the configuration of a blade inspection system for a jet engine which is a measuring endoscope system in accordance with a practical embodiment of the present invention.

FIG. 30 is a diagram showing the system configuration of the inspection system for inspecting blades. The inspection system comprises a bore scope 101, a TV camera 102, a turning tool 103, a controller 104, and a measuring apparatus 3 identical to the one shown in FIG. 1 or 2. An object to be inspected is the blades 105 of a turbine 100 (See FIGS. 31A and 31B).

Figure 31A:
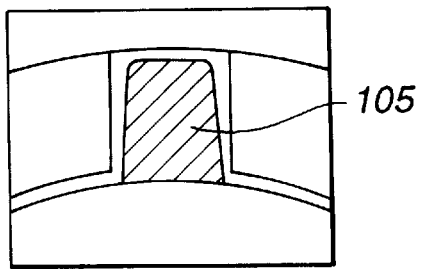
FIG. 31A is a diagram showing an image of a blade produced by the blade inspection system shown in FIG. 30, and located at a reference position.
Figure 31B:
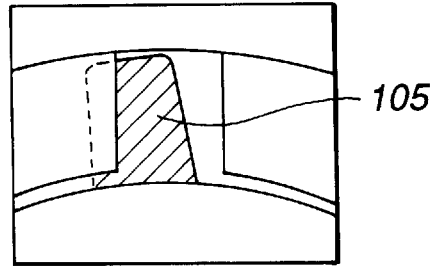
FIG. 31B is a diagram showing an image of the blade produced by the blade inspection system shown in FIG. 30 when blades are turned.

An image taken by the TV camera 102 is input to the measuring apparatus 3, and the image data is processed by a computer. An image of a blade 105 that must be stopped for inspection is recorded in advance as a reference blade image in the computer. FIG. 31A is a diagram showing the reference blade image to be displayed on the monitor 14. FIG. 31B is a diagram showing an image of one of the blades 105 being turned.

An endoscopic image is matched as a pattern with the recorded reference blade image. When a coefficient of a normalization correlation that is regarded as a scale indicating the degree of correspondence reaches a maximum, a stop signal for stopping the turning tool 103 is sent from the measuring apparatus 3 to the controller 104. The blades 105 are stopped with a given blade 105 visualized. After a given time interval elapsed, a turn signal is sent to the controller. Then, the next blade 105 is inspected.

The foregoing inspection system can overcome the aforesaid drawback of the known system. Thus, the inspection system can offer excellent workability in inspecting blades. According to a variant of this embodiment, images of blades 105 are recorded automatically. According to another variant, a defect of a blade can be inspected automatically by comparing the image of the blade with a reference image. The variants can drastically improve inspection efficiency.

According to the present invention, it is apparent that a wide range of different embodiments can be constructed on the basis of this invention without a departure from the spirit and scope of the invention. The present invention is limited to the appended claims but not restricted to any specified embodiments.

What is claimed is:

1. A measuring endoscope system, comprising:
   a main endoscope unit having a distal portion;
   an optical adaptor freely attachable or detachable to or from the distal portion of the main endoscope unit, the optical adaptor having two objective optical systems each having an optical axis;

an imaging device in said main endoscope unit optically coupled to the optical adaptor, wherein two images taken by the two objective optical systems are formed at different positions on the imaging device; and a measuring means for reading from a recording medium reference optical data specific to the optical adaptor, the reference optical data having been obtained by mounting the optical adaptor to a reference imaging device, the measuring means further for comparing the reference optical data and optical data obtained when said optical adaptor is mounted to the endoscope to produce a coordinate conversion table corresponding to the endoscope with the optical adaptor attached thereto, the measuring means further for performing coordinate conversion on images taken by the endoscope with the optical adaptor attached thereto on the basis of the coordinate conversion table, and the measuring means for calculating three-dimensional coordinates of any points in the two images by matching the images which have undergone coordinate conversion.

2. A measuring endoscope system according to claim 1, wherein f numbers rating the two objective optical systems and depending on focal lengths therefrom are substantially the same as each other.

3. A measuring endoscope system according to claim 1, wherein f numbers rating the two objective optical systems and depending on focal lengths therefrom are different.

4. A measuring endoscope system according to claim 1, wherein the optical axes of the two objective optical systems are substantially parallel to a longitudinal axis of the main endoscope unit.

5. A measuring endoscope system according to claim 1, wherein the optical axes of the two objective optical systems are oblique to a longitudinal axis of the main endoscope unit.

6. A measuring endoscope system according to claim 1, wherein the reference optical data specific to the optical adaptor includes at least a geometric distortion correction table used to correct geometric distortions caused by the two optical systems, coordinates of the optical axes of the two optical systems on the reference imaging system, and position information of reference images taken by the two optical systems and formed on the reference imaging system.

7. A measuring endoscope system according to claim 1, wherein the reference optical data specific to the optical adaptor includes at least a geometric distortion correction table used to correct geometric distortions caused by the two optical systems, coordinates of the optical axes of the two optical system on the reference imaging system, position information of reference images taken by the two optical systems and formed on the reference imaging system, and focal lengths from the two optical systems.

8. A measuring endoscope system according to claim 1, wherein the reference optical data specific to the optical adaptor includes at least a geometric distortion correction table used to correct geometric distortions caused by the two optical systems, coordinates of the optical axes of the two optical systems on the reference imaging system, position information of reference images taken by the two optical systems and formed on the reference imaging system, focal lengths from the two optical systems, a distance between the optical axes of the two optical systems, and coordinates of centers of the geometric distortions caused by the two optical systems.

9. A measuring endoscope system according to claim 1, wherein the reference optical data specific to the optical adaptor includes at least parameters listed in a geometric distortion correction table used to correct geometric distortions caused by the two optical systems, coordinates of the optical axes of the two optical systems on the reference imaging system, position information of reference images taken by the two optical systems and formed on the reference imaging system, focal lengths from the two optical systems, and a distance between the optical axes of the two optical systems.

10. A measuring endoscope system according to claim 1, wherein said objective optical systems arranged in said optical adaptor are fixed by means of an adhesive.

11. A measuring endoscope system, comprising:

a main endoscope unit having a distal portion;

an optical adaptor freely attachable or detachable to or from the distal portion of the main endoscope unit, the optical adaptor having two objective optical systems each of which have an optical axis and imaging device in said main endoscope unit and forming two images taken by the two objective optical systems at different positions on the imaging device; and a measuring means for:

reading information from a recording medium, the information including position of reference images formed on the imaging device, a geometric distortion correction table used to correct geometric distortions caused by the two objective optical systems, focal lengths, and position information of the optical axes of the two objective optical systems, the information being recorded on the recording medium when the optical adaptor is attached to a first jig;

calculating a magnitude of mismatch of a difference in position by comparing the positions of the two images formed on the imaging device with position information recorded on said recording medium when said optical adaptor is attached to a second endoscope;

creating a real correction table by correcting coordinates listed in the geometric distortion correction table on the basis of the calculated magnitude of mismatch or the difference in position;

performing coordinate conversion on the two images produced by said imaging device on the basis of the real correction table; and calculating three-dimensional coordinates of any points in the two images by matching the two images which have undergone coordinate conversion.

12. A measuring endoscope system according to claim 11, wherein f numbers rating the two objective optical systems and depending on focal lengths therefrom are substantially the same as each other.

13. A measuring endoscope system according to claim 11, wherein f numbers rating the two objective optical systems and depending on focal lengths therefrom are different.

14. A measuring endoscope system according to claim 11, wherein the optical axes of the two objective optical systems are substantially parallel to a longitudinal axis of the main endoscope unit.

15. A measuring endoscope system according to claim 11, wherein the optical axes of said two objective optical systems are oblique to a longitudinal axis of the main endoscope unit.

16. A measuring endoscope system according to claim 10, wherein, the magnitude of mismatch or a difference in position is calculated by matching patterns of the two images of a substantially white object and the position information recorded on the recording medium.

17. A measuring endoscope system according to claim 10, wherein when the three-dimensional coordinates of any points are calculated by matching the two images, a scale indicating reliability of the matching is displayed on a monitor screen.

18. A measuring endoscope system according to claim 16, wherein when the scale indicting reliability of matching two images is smaller than a threehold value, a matching mode is switched to manual matching.

19. A measuring endoscope system according to claim 10, wherein for matching the two images, only one of the two images used to designate a matching point is displayed on a monitor screen.

20. A measuring endoscope system according to claim 10, wherein for matching the two images, a first matching point is designated in one of the two images, and a second matching point in the other image is searched for automatically within an area on an epi-polar line a width of which includes a tolerance.

21. A measuring endoscope system according to claim 11, wherein for matching the two images, matching points in the images are manually designated.

22. A measuring endoscope system according to claim 11, wherein for matching two images, a first matching point is designated in one of the two images, and a second matching point in the other image is searched for in such a manner that after a probable matching point in the other image is manually designated, the second matching point is searched for within a range having the designated probable matching point as a center with a tolerance of ±10 pixels in x and y directions.

23. A measuring endoscope system according to claim 11, wherein said objective optical systems arranged in said optical adaptor are fixed by means of an adhesive.

24. A method of operating a measuring endoscope system comprising the steps of:

reading optical data from a recording medium, the optical data including optical position information concerning an optical adaptor and geometric distortion correction information;

reading image data concerning a reference object that serves as a reference, wherein the image data of the reference object is image data of a white object;

calculating a difference in position between images produced by said optical adaptor and an endoscope to which said optical adaptor is attached on the basis of the optical position information and the image data of the reference object;

creating a conversion table used to correct geometric distortions on the basis of the calculated difference in position between images and the geometric distortion correction information specific to said optical adaptor;

performing coordinate conversion on image data of an object to be measured on the basis of the conversion table;

calculating three-dimensional coordinates by matching the image data which has undergone coordinate conversion with the image data of the reference object; and measuring the object to be measured on the basis of calculated three-dimensional coordinates.

* * * * *